United States Patent [19]
Heller et al.

[11] Patent Number: 6,048,690
[45] Date of Patent: Apr. 11, 2000

[54] METHODS FOR ELECTRONIC FLUORESCENT PERTURBATION FOR ANALYSIS AND ELECTRONIC PERTURBATION CATALYSIS FOR SYNTHESIS

[75] Inventors: Michael J. Heller, Encinitas; Eugene Tu, San Diego; Ronald G. Sosnowski, Coronado; James P. O'Connell, Del Mar, all of Calif.

[73] Assignee: Nanogen, Inc., San Diego, Calif.

[21] Appl. No.: 08/855,058

[22] Filed: May 14, 1997

Related U.S. Application Data

[63] Continuation-in-part of application No. 08/534,454, Sep. 27, 1995, Pat. No. 5,849,486, which is a continuation-in-part of application No. 08/304,657, Sep. 9, 1994, Pat. No. 5,632,957, which is a continuation-in-part of application No. 08/271,882, Jul. 7, 1994, which is a continuation-in-part of application No. 08/146,504, Nov. 1, 1993, Pat. No. 5,605,662, and application No. 08/703,601, Aug. 23, 1996, Pat. No. 5,849,489, which is a continuation of application No. 08/232,233, May 5, 1994, Pat. No. 5,565,322, which is a continuation-in-part of application No. 07/790,262, Nov. 7, 1991, Pat. No. 5,532,129, and a continuation of application No. 08/250,951, May 27, 1994, and application No. 08/258,168, Aug. 25, 1994, Pat. No. 5,787,032.

[51] Int. Cl.$^7$ ..................................................... C12Q 1/68
[52] U.S. Cl. ................................. 435/6; 436/501; 422/50; 422/68.1; 422/69; 422/82.05; 422/82.06; 422/82.07; 422/82.08; 422/129
[58] Field of Search .............................. 422/50, 68.1, 69, 422/82.05, 82.06, 82.07, 82.08, 129; 435/6, 810; 436/501; 935/77, 78

[56] References Cited

U.S. PATENT DOCUMENTS

| | | | |
|---|---|---|---|
| 3,950,738 | 4/1976 | Hayashi et al. | 340/173 LS |
| 3,995,190 | 11/1976 | Salgo | 313/391 |

(List continued on next page.)

FOREIGN PATENT DOCUMENTS

| | | |
|---|---|---|
| 0228075 | 7/1987 | European Pat. Off. . |
| 2156074 | 10/1985 | United Kingdom . |

(List continued on next page.)

OTHER PUBLICATIONS

Matthews et al. (1988) Analytical Biochemistry, vol. 169, pp. 1–25.

(List continued on next page.)

*Primary Examiner*—Ardin H. Marschel
*Attorney, Agent, or Firm*—Lyon & Lyon LLP

[57] ABSTRACT

Methods for electronic perturbation of fluorescence, chemiluminescence and other emissive materials provide for molecular biological analysis. In a preferred method for hybridization analysis of a sample, an electronic stringency control device is used to perform the steps of: providing the sample, a first probe with a fluorescent label and a second probe with a label under hybridization conditions on the electronic stringency control device, forming a hybridization product, subjecting the hybridization product to an electric field force, monitoring the fluorescence from the hybridization product, and analyzing the fluorescent signal. The label preferably serves as a quencher for the fluorescent label. In yet another aspect of this invention, a method for achieving electronic fluorescence perturbation on an electronic stringency control device comprising the steps of: locating a first polynucleotide and a second polynucleotide adjacent the electronic stringency control device, the first polynucleotide and second polynucleotide being complementary over at least a portion of their lengths and forming a hybridization product, the hybridization product having an associated environmental sensitive emission label, subjecting the hybridization product and label to a varying electrophoretic force, monitoring the emission from the label, and analyzing the monitored emission to determine the electronic fluorescence perturbation effect. In yet another aspect of this invention, a method is provided for electronic perturbation catalysis of substrate molecules on an electronic control device containing at least one microlocation comprising the steps of: immobilizing on the microlocation an arrangement of one or more reactive groups, exposing the reactive groups to a solution containing the substrate molecules of interest, and applying an electronic pulsing sequence which causes charge separation between the reactive groups to produce a catalytic reaction on the substrate molecules.

46 Claims, 12 Drawing Sheets

U.S. PATENT DOCUMENTS

| | | | |
|---|---|---|---|
| 4,563,419 | 1/1986 | Ranki et al. | 435/6 |
| 4,580,895 | 4/1986 | Patel | 356/39 |
| 4,584,075 | 4/1986 | Goldstein | 204/182.4 |
| 4,594,135 | 6/1986 | Goldstein | 204/551 |
| 4,751,177 | 6/1988 | Stabinsky | 435/6 |
| 4,787,963 | 11/1988 | MacConnell | 204/180.1 |
| 4,816,418 | 3/1989 | Mack et al. | 436/518 |
| 4,822,566 | 4/1989 | Newman | 422/68 |
| 4,908,112 | 3/1990 | Pace | 204/299 R |
| 5,063,081 | 11/1991 | Cozzette et al. | 427/2 |
| 5,075,077 | 12/1991 | Durley, II et al. | 422/56 |
| 5,096,669 | 3/1992 | Lauks et al. | 422/61 |
| 5,096,807 | 3/1992 | Leaback | 435/6 |
| 5,125,748 | 6/1992 | Bjornson et al. | 356/414 |
| 5,126,022 | 6/1992 | Soane et al. | 204/180.1 |
| 5,143,854 | 9/1992 | Pirrung et al. | 436/518 |
| 5,164,319 | 11/1992 | Hafeman et al. | 435/291 |
| 5,166,063 | 11/1992 | Johnson | 435/173 |
| 5,200,051 | 4/1993 | Cozzette et al. | 204/403 |
| 5,202,231 | 4/1993 | Drmanac et al. | 435/6 |
| 5,219,726 | 6/1993 | Evans | 435/6 |
| 5,227,265 | 7/1993 | DeBoer et al. | 430/41 |
| 5,234,566 | 8/1993 | Osman et al. | 204/403 |
| 5,304,487 | 4/1994 | Wilding et al. | 435/291 |
| 5,312,527 | 5/1994 | Mikkelsen et al. | 204/153.12 |
| 5,434,049 | 7/1995 | Okano et al. | 435/6 |
| 5,516,698 | 5/1996 | Begg et al. | 436/89 |
| 5,532,129 | 7/1996 | Heller | 435/6 |
| 5,565,322 | 10/1996 | Heller | 435/6 |
| 5,605,662 | 2/1997 | Heller et al. | 422/68.1 |
| 5,605,839 | 2/1997 | Simpson et al. | 436/89 |
| 5,632,957 | 5/1997 | Heller et al. | 422/68.1 |
| 5,681,751 | 10/1997 | Begg et al. | 436/89 |
| 5,787,032 | 7/1998 | Heller et al. | 365/151 |
| 5,849,486 | 12/1998 | Heller et al. | 435/6 |
| 5,849,489 | 12/1998 | Heller | 435/6 |
| 5,853,668 | 12/1998 | Begg et al. | 422/82.02 |

FOREIGN PATENT DOCUMENTS

| | | |
|---|---|---|
| WO86/03782 | 7/1986 | WIPO . |
| WO88/08528 | 11/1988 | WIPO . |
| WO89/01159 | 2/1989 | WIPO . |
| WO89/10977 | 11/1989 | WIPO . |
| WO90/01564 | 2/1990 | WIPO . |
| WO92/04470 | 3/1992 | WIPO . |
| WO93/22678 | 11/1993 | WIPO . |
| WO95/07363 | 3/1995 | WIPO . |
| 57087 | of 1987 | Yugoslavia . |

OTHER PUBLICATIONS

Anand and Southern "Pulsed Field Gel Electrophoresis," *Gel Electrophoresis of Nucleic Acids —A Practical Approach*, 2d. Ed., D. Rickwood and B.D. Hames (New York:IRL Press 1990), pp. 101–123.

Anderson and Young, "Quantitive Filter Hybridization," *Nucleic Acid Hybridization —A Practical Approach*, Eds. B.D. Hames and S.J. Higgins (Washington, D.C.:IRL Press 1985) pp. 73–111.

Bains, "Setting a Sequence to Sequence a Sequence," *Bio/Technology*, 10:757–758 (1992).

Barinaga, "Will 'DNA Chip' Speed Genome Initative?", *Science*, 253:1489 (1991).

Beattie et al., "Genosensor Technology," *The 1992 San Diego Conference: Genetic Recognition*, pp. 1–5 (Nov, 1992).

Beltz et al., "Isolation of Multigene Families and Determination of Homologies by Filter Hybrizidization Methods," *Methods in Enzymology*, 100:266–285 (1983).

Conner et al., "Detection of Sickle Cell $\beta^3$–Globin Allele by Hybridization With Synthetic Oligonucleotides," *Proc. Natl. Acad, Sci. USA*, 80:278–282 (1983).

Drmanac et al. "Sequencing of Megabase Plus DNA by Hybridization: Theory of the Method," *Genomics*, 4:114–128 (1989).

Drmanac et al., "DNA Sequence Determination by Hybridixation: A Strategy for Efficient Large–Scale Sequencing," *Science*, 260: 1649–1652 (1993).

Fodor et al., "Multiplexed Biochemical Assays With Biological Chips," *Nature*, 364:555–556 (1993).

Fodor et al., "Light–Directed, Spatially Addressable Parallel Chemical Synsthesis," *Science*, 251:767–773 (1992).

Horejsi, "Some Theoretical Aspects of Affinity Electrophoresis," *Journal of Chromatography*, 178:1–13 (1979).

Horejsi et al., Determining of Dissociation Constants of Lectin Sugar Complexes by Means of Affinity Electrophoresis, *Biochimica at Biophysica Acta*, 499:200–300 (1977).

Ranki et al., "Sandwich Hybridization as a Convenient Method for the Detection of Nucleic Acids in Crude Samples," *Gene*, 21:77–85 (1983).

Saiki, "Amplification of Genomic DNA, " *PCR Protocols: A Guide to Methods and Applications*, (Academic Press, Inc. 1990), pp 13–20.

Southern et al., "Analyzing and Comparing Nucleic Sequences by Hybridization to Arrays of Oligonucleotides Evaluation Using Experimental Models," *Genomics*, 13:1008–1017 (1992).

Strezoska et al., "DNA Sequencing by Hybridization: 100 Bases Read by a Non–Gel–Based Method", *Proc. Natl. Acad. Sci. USA*, 88:10089–93 (1991).

Wallace et al., "Hybridization of Synthetic Oligedexribonucleotides to Øx174 DNA: The Effect of Single Base Pair Mismatch," *Nucleic Acid Res.*, 6:3543–3557 (1979).

Washizu, "Electrostatic Manipulation of Biological Objects," *Journal of Electrostatics*, 25:109–123 (1990).

Washizu and Kurosawa, "Electrostatic Manipulation of DNA in Microfabricated Structures," *IEEE Transactions on Industry Applications*, 26:1165–1172 (1990).

Brown et al., "Electrochemically Induced Adsorption of Radio–Labelled DNA on Gold and HOPG Substrates for STM Investigations", *Ultramicroscopy*, 38 (1991) pp 253–264.

Palacek, "New Trends in Electrochemical Analysis of Nucleic Acids", *Bioelectrochemistry and Bioenergetics*, 20 (1988) pp 179–194.

RAS G 22MERS

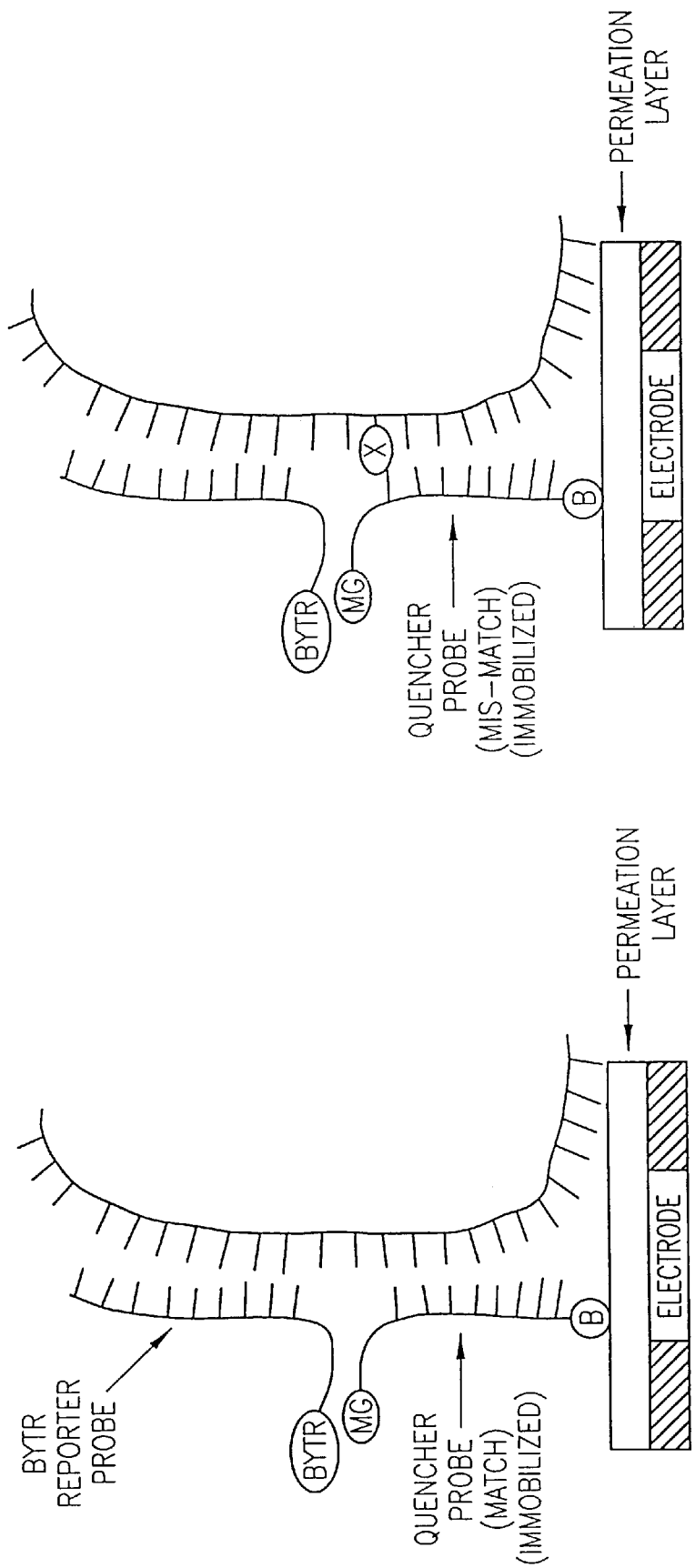

SEQUENCE LISTING

<160> NUMBER OF SEQ ID NOS: 20

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthesized
      probe

<400> SEQUENCE: 1 aaatttaat atataat                                                    17

```
<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthesized
      probe

<400> SEQUENCE: 2
ccacgtagaa ctgctcatc                                                    19

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:
      Buffer-containing peptide structure

<400> SEQUENCE: 3

Gly His Phe Cys Phe Gly
  1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:
      Buffer-containing peptide structure

<400> SEQUENCE: 4

Gly His Pro Cys Pro Gly
  1               5

<210> SEQ ID NO 5
<211> LENGTH: 22
<212> TYPE: DNA
<213> ORGANISM: Human RAS

<400> SEQUENCE: 5
gcccacaccg ccggcgccca cc                                                22

<210> SEQ ID NO 6
<211> LENGTH: 22
<212> TYPE: DNA
<213> ORGANISM: Human RAS

<400> SEQUENCE: 6
ggtgggcgcc ggcggtgtgg gc                                                22

<210> SEQ ID NO 7
<211> LENGTH: 22
<212> TYPE: DNA
<213> ORGANISM: Human RAS

<400> SEQUENCE: 7
ggtgggcgcc ggaggtgtgg gc                                                22

<210> SEQ ID NO 8
<211> LENGTH: 19
<212> TYPE: DNA
<213> ORGANISM: Human HLA

<400> SEQUENCE: 8
```

```
ccacgtagaa ctgctcatc                                                19

<210> SEQ ID NO 9
<211> LENGTH: 19
<212> TYPE: DNA
<213> ORGANISM: Human HLA

<400> SEQUENCE: 9
gatgagcagt tctacgtgg                                                19

<210> SEQ ID NO 10
<211> LENGTH: 19
<212> TYPE: DNA
<213> ORGANISM: Human HLA

<400> SEQUENCE: 10
gatgagcagc tctacgtgg                                                19

<210> SEQ ID NO 11
<211> LENGTH: 19
<212> TYPE: DNA
<213> ORGANISM: Human HLA

<400> SEQUENCE: 11
tatgagcagt tctacgtgg                                                19

<210> SEQ ID NO 12
<211> LENGTH: 19
<212> TYPE: DNA
<213> ORGANISM: Human HLA

<400> SEQUENCE: 12
gatgagcagt tctacgtgt                                                19

<210> SEQ ID NO 13
<211> LENGTH: 19
<212> TYPE: DNA
<213> ORGANISM: Human HLA

<400> SEQUENCE: 13
gatgagcagt tctacgtgg                                                19

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Quencher
      acceptor target probes

<400> SEQUENCE: 14
cacgagagac tcatgagcag gggctagccg atcgggtcct caggtcaagt c            51

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Quencher
      acceptor target probes

<400> SEQUENCE: 15
cacgagagac tcatgagcag gcgctagccg atcgggtcct caggtcaagt c            51
```

```
<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence:  Quencher
      acceptor target probes

<400> SEQUENCE: 16
cacgagagac tcatgagcag gggctagcca atcgggtcct caggtcaagt c            51

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence:  Quencher
      acceptor target probes

<400> SEQUENCE: 17
cacgagagac tcatgagcag gggctagcca accgggtcct caggtcaagt c            51

<210> SEQ ID NO 18
<211> LENGTH: 48
<212> TYPE: DNA
<213> ORGANISM: Artificial Sequence
<220> FEATURE:
<223> OTHER INFORMATION: Description of Artificial Sequence:  Quencher
      acceptor target probes

<400> SEQUENCE: 18
gcacctgact cctgaggaga agtcccgatc gggtcctcag gtcaagtc                48

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Energy
      Transfer Probes

<400> SEQUENCE: 19
tgacctgagg acccgatcg                                                19

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:  Energy
      Transfer Probes

<400> SEQUENCE: 20
agcccctgct catgagtctc t                                             21
```

METHODS FOR ELECTRONIC FLUORESCENT PERTURBATION FOR ANALYSIS AND ELECTRONIC PERTURBATION CATALYSIS FOR SYNTHESIS

RELATED APPLICATION INFORMATION

This application is a continuation-in-part application of application Ser. No. 08/534,454, filed Sep. 27, 1995, entitled "Methods for Hybridization Analysis Utilizing Electrically Controlled Hybridization" U.S. Pat. No. 5,849,486, which is a continuation-in-part of application Ser. No. 08/304,657, filed Sep. 9, 1994, entitled, as amended, "Molecular Biological Diagnostic Systems Including Electrodes", U.S. Pat. No. 5,632,957, which is a continuation-in-part of application Ser. No. 08/271,882, filed Jul. 7, 1994, entitled, as amended, "Methods for Electronic Stringency Control for Molecular Biological Analysis and Diagnostics", now allowed, which is a continuation-in-part of application Ser. No. 08/146,504, filed Nov. 1, 1993, entitled, as amended, "Active Programmable Electronic Devices for Molecular Biological Analysis and Diagnostics", U.S. Pat. No. 5,605,662, and also application Ser. No. 08/703,601, filed Aug. 23, 1996, entitled "Hybridization of Polynucleotide Conjugated with Chromophores and Fluorophores to Generate Donor-to-Donor Energy Transfer System", U.S. Pat. No. 5,849,489, which is a continuation of application Ser. No. 08/232,233, filed May 5, 1994, entitled "Hybridization of Polynucleotide Conjugated with Chromophores and Fluorophores to Generate Donor-to-Donor Energy Transfer System", now issued as U.S. Pat. No. 5,565,322, which is a continuation-in-part of application Ser. No. 07/790,262, filed Nov. 7, 1991, entitled "Self-Organizing Molecular Photonic Structures Based on Chromophore- and Fluorophore-Containing Polynucleotide and Methods of Their Use", now issued as U.S. Pat. No. 5,532,129 (via continuation application Ser. No. 08/250,951, filed May 27, 1994) and also application Ser. No. 08/258,168, filed Aug. 25, 1994, entitled "DNA Optical Storage", now issued as U.S. Pat. No. 5,787,032, all incorporated herein by reference as if fully set forth herein.

FIELD OF THE INVENTION

This invention relates to systems, devices, methods, and mechanisms for performing multi-step molecular biological analysis, nucleic acid hybridization reactions, nucleic acid sequencing, and the catalysis of biomolecular, organic and inorganic reactions. More particularly, the molecular biological type analysis involves electronic fluorescent perturbation mechanisms for the detection of DNA hybrids, point mutations, deletions or repeating sequences in nucleic acid hybridization reactions, electronic fluorescent perturbation mechanisms for sequencing of DNA and RNA molecules, and electric field based catalytic mechanisms for biomolecular, biopolymer and other chemical reactions.

BACKGROUND OF THE INVENTION

Molecular biology comprises a wide variety of techniques for the analysis of nucleic acid and protein. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e.g., J. Sambrook, E. F. Fritsch, and T. Maniatis, *Molecular Cloning: A Laboratory Manual,* 2 Ed., Cold spring Harbor Laboratory Press, Cold Spring Harbor, N.Y., 1989).

Most of these techniques involve carrying out numerous operations (e.g., pipetting, centrifugations, electrophoresis) on a large number of samples. They are often complex and time consuming, and generally require a high degree of accuracy. Many a technique is limited in its application by a lack of sensitivity, specificity, or reproducibility. For example, these problems have limited many diagnostic applications of nucleic acid hybridization analysis.

The complete process for carrying out a DNA hybridization analysis for a genetic or infectious disease is very involved. Broadly speaking, the complete process may be divided into a number of steps and substeps. In the case of genetic disease diagnosis, the first step involves obtaining the sample (blood or tissue). Depending on the type of sample, various pre-treatments would be carried out. The second step involves disrupting or lysing the cells, which then release the crude DNA material along with other cellular constituents. Generally, several sub-steps are necessary to remove cell debris and to purify further the crude DNA. At this point several options exist for further processing and analysis. One option involves denaturing the purified sample DNA and carrying out a direct hybridization analysis in one of many formats (dot blot, microbead, microliter plate, etc.). A second option, called Southern blot hybridization, involves cleaving the DNA with restriction enzymes, separating the DNA fragments on an electrophoretic gel, blotting to a membrane filter, and then hybridizing the blot with specific DNA probe sequences. This procedure effectively reduces the complexity of the genomic DNA sample, and thereby helps to improve the hybridization specificity and sensitivity. Unfortunately, this procedure is long and arduous. A third option is to carry out the polymerase chain reaction (PCR) or other amplification procedure. The PCR procedure amplifies (increases) the number of target DNA sequences. Amplification of target DNA helps to overcome problems related to complexity and sensitivity in genomic DNA analysis. All these procedures are time consuming, relatively complicated, and add significantly to the cost of a diagnostic test. After these sample preparation and DNA processing steps, the actual hybridization reaction is performed. Finally, detection and data analysis convert the hybridization event into an analytical result.

The steps of sample preparation and processing have typically been performed separate and apart from the other main steps of hybridization and detection and analysis. Indeed, the various substeps comprising sample preparation and DNA processing have often been performed as a discrete operation separate and apart from the other substeps. Considering these substeps in more detail, samples have been obtained through any number of means, such as obtaining of full blood, tissue, or other biological fluid samples. In the case of blood, the sample is processed to remove red blood cells and retain the desired nucleated (white) cells. This process is usually carried out by density gradient centrifugation. Cell disruption or lysis is then carried out, preferably by the technique of sonication, freeze/thawing, or by addition of lysing reagents. Crude DNA is then separated from the cellular debris by a centrifugation step. Prior to hybridization, double-stranded DNA is denatured into single-stranded form. Denaturation of the double-stranded DNA has generally been performed by the techniques involving heating (>Tm), changing salt concentration, addition of base (NaOH), or denaturing reagents (urea, formamide, etc.). Workers have suggested denaturing DNA into its single-stranded form in an electrochemical cell. The theory is stated to be that there is electron transfer to the DNA at the interface of an electrode, which effectively weakens the double-stranded structure and results in separation of the strands. See, generally, Stanley, "DNA Denaturation by an Electric Potential", U.K. patent application 2,247,889 published Mar. 18, 1992.

Nucleic acid hybridization analysis generally involves the detection of a very small number of specific target nucleic acids (DNA or RNA) with an excess of probe DNA, among a relatively large amount of complex non-target nucleic acids. The substeps of DNA complexity reduction in sample preparation have been utilized to help detect low copy numbers (i.e. 10,000 to 100,000) of nucleic acid targets. DNA complexity is overcome to some degree by amplification of target nucleic acid sequences using polymerase chain reaction (PCR). (See, M. A. Innis et al, *PCR Protocols: A Guide to Methods and Applications*, Academic Press, 1990). While amplification results in an enormous number of target nucleic acid sequences that improves the subsequent direct probe hybridization step, amplification involves lengthy and cumbersome procedures that typically must be performed on a stand alone basis relative to the other substeps. Substantially complicated and relatively large equipment is required to perform the amplification step.

The actual hybridization reaction represents the most important and central step in the whole process. The hybridization step involves placing the prepared DNA sample in contact with a specific reporter probe, at a set of optimal conditions for hybridization to occur to the target DNA sequence. Hybridization may be performed in any one of a number of formats. For example, multiple sample nucleic acid hybridization analysis has been conducted on a variety of filter and solid support formats (See G. A. Beltz et al., in *Methods in Enzymology*, Vol. 100, Part B, R. Wu, L. Grossman, K. Moldave, Eds., Academic Press, New York, Chapter 19, pp. 266–308, 1985). One format, the so-called "dot blot" hybridization, involves the non-covalent attachment of target DNAs to filter, which are subsequently hybridized with a radioisotope labeled probe(s). "Dot blot" hybridization gained wide-spread use, and many versions were developed (see M. L. M. Anderson and B. D. Young, in *Nucleic Acid Hybridization—A Practical Approach*, B. D. Hames and S. J. Higgins, Eds., IRL Press, Washington, D.C. Chapter 4, pp. 73–111, 1985). It has been developed for multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

New techniques are being developed for carrying out multiple sample nucleic acid hybridization analysis on micro-formatted multiplex or matrix devices (e.g., DNA chips) (see M. Barinaga, 253 Science, pp. 1489, 1991; W. Bains, 10 Bio/Technology, pp. 757–758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

The micro-formatted hybridization can be used to carry out "sequencing by hybridization" (SBH) (see M. Barinaga, 253 Science, pp. 1489, 1991; W. Bains, 10 Bio/Technology, pp. 757–758, 1992). SBH makes use of all possible n-nucleotide oligomers (n-mers) to identify n-mers in an unknown DNA sample, which are subsequently aligned by algorithm analysis to produce the DNA sequence (R. Drmanac and R. Crkvenjakov, Yugoslav Patent Application No. 570/87, 1987; R. Drmanac et al., 4 Genomics, 114, 1989; Strezoska et al., 88 Proc. Natl. Acad. Sci. USA 10089, 1992; and R. Dramanac and R. B. Crkvenjakov, U.S. Pat. No. 5,202,231, Apr. 13, 1993).

There are two formats for carrying out SBH. The first format involves creating an array of all possible n-mers on a support, which is then hybridized with the target sequence. The second format involves attaching the target sequence to a support, which is sequentially probed with all possible n-mers. Both formats have the fundamental problems of direct probe hybridizations and additional difficulties related to multiplex hybridizations.

Southern, United Kingdom Patent Application GB 8810400, 1988; E. M. Southern et al., 13 Genomics 1008, 1992, proposed using the first format to analyze or sequence DNA. Southern identified a known single point mutation using PCR amplified genomic DNA. Southern also described a method for synthesizing an array of oligonucleotides on a solid support for SBH. However, Southern did not address how to achieve optimal stringency condition for each oligonucleotide on an array.

Concurrently, Drmanac et al., 260 Science 1649–1652, 1993, used the second format to sequence several short (116 bp) DNA sequences. Target DNAs were attached to membrane supports ("dot blot" format). Each filter was sequentially hybridized with 272 labeled 10-mer and 11-mer oligonucleotides. A wide range of stringency condition was used to achieve specific hybridization for each n-mer probe; washing times varied from 5 minutes to overnight, and temperatures from 0° C. to 16° C. Most probes required 3 hours of washing at 16° C. The filters had to be exposed for 2 to 18 hours in order to detect hybridization signals. The overall false positive hybridization rate was 5% in spite of the simple target sequences, the reduced set of oligomer probes, and the use of the most stringent conditions available.

A variety of methods exist for detection and analysis of the hybridization events. Depending on the reporter group (fluorophore, enzyme, radioisotope, etc.) used to label the DNA probe, detection and analysis are carried out fluorometrically, colorimetrically, or by autoradiography. By observing and measuring emitted radiation, such as fluorescent radiation or particle emission, information may be obtained about the hybridization events. Even when detection methods have very high intrinsic sensitivity, detection of hybridization events is difficult because of the background presence of non-specifically bound materials.

In the many applications of DNA hybridization for research and diagnostics, the most difficult analysis involve the differentiation of a single base mismatch from a match target sequence. This is because the analysis involves discriminating a small difference in one hybridized pair, the mismatch, from the match. The teachings of this invention are of particular relevance to these problems.

SUMMARY OF THE INVENTION

As a main aspect of this invention, it has been surprisingly discovered that the fluorescence signal obtained during the electronic denaturation or dehybridization of DNA hybrids is perturbed at or around the electronic power (current and voltage) levels which are associated with the denaturation or dehybridization process. In one embodiment, the fluorescence signal perturbation phenomena appears as a rise or spike in fluorescence intensity prior to dehybridization of a fluorescent labeled probe from a capture sequence attached to the microlocation test site. The power level, amplitude and slope of this fluorescence spike provide analytical tools for diagnosis. The combination of the fluorescence perturbation with other measurements also indicative of the hybridization match/mismatch state, such as consideration of the electronic melting (50% fluorescence decrease during electronic stringency control) can in combination provide a more efficient and reliable hybridization match/mismatch analysis.

In general, this controlled dehybridization or electronic stringency process results in a significant differential between the final fluorescent intensity values for the match versus the mismatch sequence. This difference in fluorescent intensity values is used to determine a discrimination ratio, which confirms and identifies that a particular mismatch was present in the sample.

It has been discovered that the fluorescent perturbation effect (FPE) provides a powerful analytical tool for DNA hybridization analysis, particularly for the near instantaneous, e.g., less than one minute, and especially less than 5 seconds, discrimination of match/mismatched DNA hybrids. Novel DNA sequencing applications are possible. New fluorescent donor/acceptor/quencher energy transfer mechanisms are created. New electronic catalytic mechanisms are created.

In one aspect, this invention relates to using precisely controlled electric or electrophoretic fields to cause or influence fluorophore or chromophore groups in special arrangements with molecular structures (such as nucleic acids), to produce rapid signal variations (perturbations) which correlate with and identify small differences in these molecular structures. In a preferred method for hybridization analysis of a sample, an electronic stringency control device is used to perform the steps of: providing the sample, a first probe with a fluorescent label and a second probe with a label under hybridization conditions on the electronic stringency control device, forming a hybridization product, subjecting the hybridization product to an electric field force, monitoring the fluorescence from the hybridization product, and analyzing the fluorescent signal. The label preferably serves as a quencher for the fluorescent label.

Most broadly, this invention relates to integrated microelectronic systems, devices, components, electronic based procedures, electronic based methods, electronic based mechanisms, and flurophore/chromophore arrangements for: (1) molecular biological and clinical diagnostic analyses; (2) nucleic acid sequencing applications; and (3) for carrying out catalysis of biomolecular, organic, and inorganic reactions.

More specifically, the molecular biological and clinical diagnostic analyses relate to the utilization of the electronic fluorescent perturbation based mechanisms for the detection and identification of nucleic acid hybrids, single base mismatches, point mutations, single nucleotide polymorphisms (SNPs), base deletions, base insertions, crossover/splicing points (translocations), intron/exon junctions, restriction fragment length polymorphisms (RFLPs), short tandem repeats (STRs) and other repeating or polymorphic sequences in nucleic acids.

More specifically, the nucleic acid sequencing applications involve utilization of the electronic fluorescent perturbation based mechanisms to elucidate base sequence information in DNA, RNA and in nucleic acid derivatives. Most particularly, to elucidate sequence information from the terminal ends of the nucleic acid molecules. This method achieves electronic fluorescence perturbation on an electronic stringency control device comprising the steps of: locating a first polynucleotide and a second polynucleotide adjacent the electronic stringency control device, the first polynucleotide and second polynucleotide being complementary over at least a portion of their lengths and forming a hybridization product, the hybridization product having an associated environmental sensitive emission label, subjecting the hybridization product and label to a varying electrophoretic force, monitoring the emission from the label, and analyzing the monitored emission to determine the electronic fluorescence perturbation effect.

More specifically, the catalytic reactions relate to the utilization of electronic based catalytic mechanisms for carrying out biomolecular, biopolymer, organic polymer, inorganic polymer, organic, inorganic, and other types of chemical reactions. Additionally, the electronic based catalytic mechanisms can be utilized for carrying out nanofabrication, and other self-assembly or self-organizational processes. This method provides for electronic perturbation catalysis of substrate molecules on an electronic control device containing at least one microlocation comprising the steps of: immobilizing on the microlocation an arrangement of one or more reactive groups, exposing the reactive groups to a solution containing the substrate molecules of interest, and applying an electronic pulsing sequence which causes charge separation between the reactive groups to produce a catalytic reaction on the substrate molecules.

More generally, the present invention relates to the design, fabrication, and uses of self-addressable self-assembling microelectronic integrated systems, devices, and components which utilize the electronic mechanisms for carrying out the controlled multi-step processing and multiplex reactions in a microscopic, semi-microscopic and macroscopic formats. These reactions include, but are not limited to, most molecular biological procedures, such as: (1) multiplex nucleic acid hybridization analysis in reverse dot blot formats, sandwich formats, homogeneous/heterogeneous formats, target/probe formats, in-situ formats, and flow cytometry formats; (2) nucleic acid, DNA, and RNA sequencing; (3) molecular biological restriction reactions, ligation reactions, and amplification type reactions; (4) immunodiagnostic and antibody/antigen reactions; (5) cell typing and separation procedures; and (6) enzymatic and clinical chemistry type reactions and assays.

In addition, the integrated systems, devices, and components which utilize electronic based catalytic mechanisms are able to carry out biomolecular, biopolymer and other types of chemical reactions: (1) based on electric field catalysis; and/or (2) based on multi-step combinatorial biopolymer synthesis, including, but not limited to, the synthesis of polynucleotides and oligonucleotides, peptides, organic molecules, bio-polymers, organic polymers, mixed biopolymers/organic polymers, two and three dimensional nanostructures, and nanostructures and micron-scale structures on or within silicon or other substrate materials.

Additionally, with respect to electronic fluorescent perturbation mechanisms, the present invention relates to unique intermolecular and intramolecular constructs and arrangements of chromophores, fluorophores, luminescent molecules or moities, metal chelates (complexes),enzymes, peptides, and amino acids, associated with nucleic acid sequences, polypeptide sequences, and/or other polymeric materials. Of particular importance being those constructs and arrangements of fluorophores and chromophores which produce fluorescent energy transfer, charge transfer or mechanical mechanisms which can be modulated or affected by electric or electrophoretic fields to produce fluorescent or luminescent signals which provide information about molecular structure.

With respect to the electronic catalytic mechanisms in homogeneous (solution) or heterogeneous (solution/solid support) formats, the present invention relates to unique intermolecular and intramolecular constructs and arrangements of chromophores, fluorophores, luminescent molecules or moities, metal chelates (complexes),enzymes, peptides, and amino acids, nucleophilic molecules or moities, electrophilic molecules or moities, general acid or base catalytic molecules or moieties, and substrate binding site molecules and moities, associated with nucleic acid sequences, polypeptide sequences, other biopolymers, organic polymers, inorganic polymers, and other polymeric materials.

Additionally, this invention relates to the utilization of electric or electrophoretic fields to induce fluorescent perturbation based mechanisms in arrangements of fluorophores and chromophores in solid state or sol-gel state optoelectronic devices and optical memory materials.

It is therefore an object of this invention to provide for methods and systems for improved detection and analysis of biological materials.

It is yet a further object of this invention to provide for methods which provide for the rapid and accurate discrimination between matches and mismatches in nucleic acid hybrids.

BRIEF DESCRIPTION OF THE DRAWINGS

FIG. 11A shows a schematic representation for the hybridized arrangement of a target probe, a labeled reporter probe and a quencher probe.

FIG. 11B shows the schematic representation of FIG. 11A with a mismatch between the target and probe.

DETAILED DESCRIPTION OF THE INVENTION

The APEX device as described in the various parent applications has been utilized in novel ways resulting in methods which improve the analytical or diagnostic capabilities of the device. It has been surprisingly discovered that the fluorescent signal is perturbed during the electronic dehybridization of DNA hybrids. This method has particular application to DNA hybridization and single-base mismatch analysis. Specifically, during electronic dehybridization, also known as stringency control or electronic stringency control, a rise or spike in the fluorescence intensity has been observed just prior to the dehybridization of the fluorescent labeled probes from capture sequences attached to the APEX chip pad.

Figure 1A:
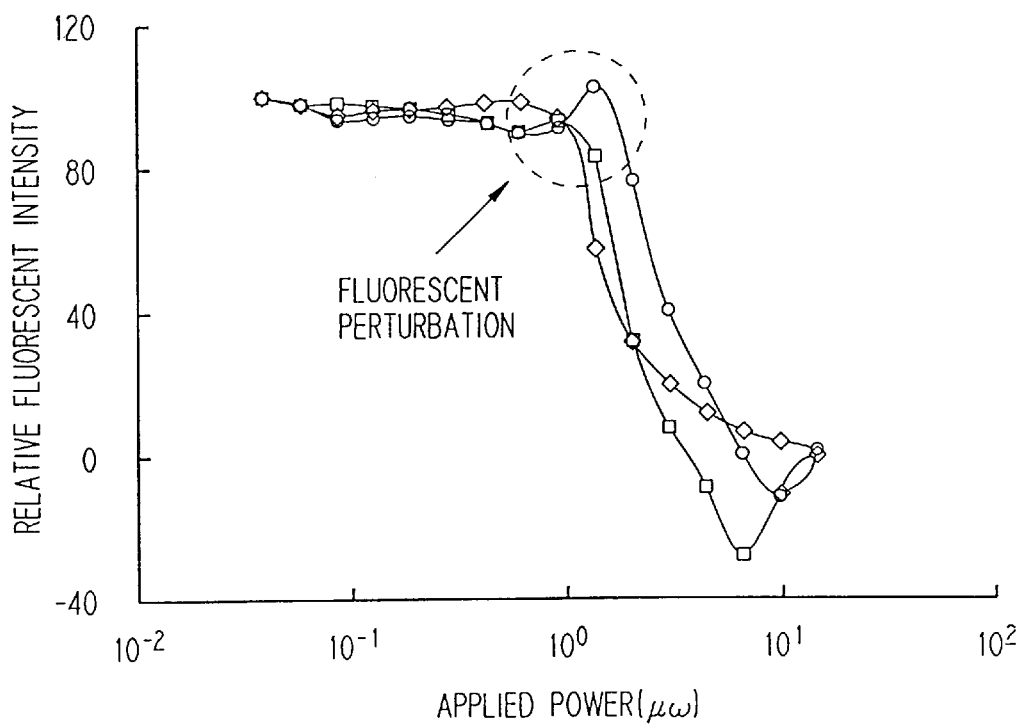
FIG. 1A is a plot of the relative fluorescent intensity as a function of applied power (microwatts) for a 20-mer oligomer duplex (100% AP).
Figure 1B:
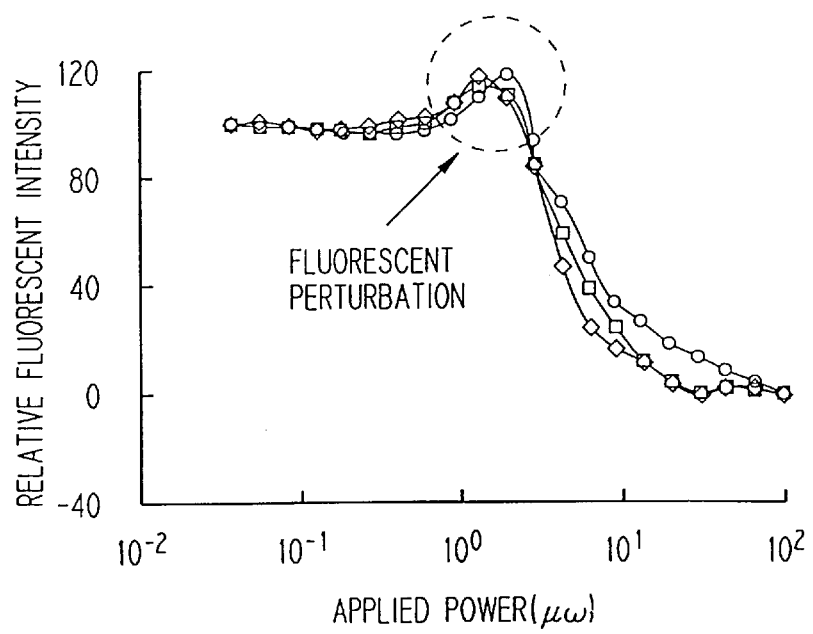
FIG. 1B is a plot of the relative fluorescent intensity versus applied power (microwatts) for a 19-mer oligomer duplex (53% GC).

FIGS. 1A and 1B show the results of electronic denaturization experiments run on an APEX chip having 25 test microlocations with 80 micron diameter utilizing platinum electrodes. For this use, the chip was overlaid with a 1 micron thick avidin/agarose permeation layer. Two 5'-labeled bodipy Texas Red (Ex 590 nm, EM 630 nm) target probes were used in the experiments. The probe of FIG. 1A was a 17 mer (5'-BYTRAAATTTTAATATATAAT-3') (SEQUENCE ID NO. 1) containing 100% AT, with a melting temperature (Tm) of 33° C. The probe of FIG. 1B was a 19 mer (5'BYTRCCACGTAGAACTGCTCATC-3') (SEQUENCE ID NO. 2) containing 53% GC, with a melting temperature (Tm) of 54° C. (Melting temperature or Tm refers to the temperature at which the dehybridization process is 50% complete). The appropriate complementary biotinylated capture sequences were attached to the avidin/agarose permeation layer over several of the test pads (on the same chip). The capture probe density was ~$10^8$ probes per pad. The fluorescent labeled target probes, at a concentration of ~1.0 $\mu$M in 50 mM sodium phosphate (pH 7.0), 500 mM NaCl were first hybridized to the attachment probes on the 5580 chips. The chips were then thoroughly washed with 20 mM NaPO4 (pH 7.0).

Electronic denaturation was then carried out by biasing the test pad negative, and increasing the power to the test pad from ~$10^{-1}$ microwatts ($\mu$W) to ~$2\times10^2$ microwatts ($\mu$W) over a 90 second time period. Three pads were tested for each of the target probes. The relative change in fluorescent intensity was plotted as a function of the increasing power. In general, the electrophoretic field, force or power necessary to dehybridize a probe from its complementary sequence correlates with the binding energy or Tm (melting temperature) for the DNA duplex. In above experiments the overall power level ($\mu$W) necessary to dehybridize the 19-mer probe with 53% GC probe (Tm of 54° C.) was higher than for the 20-mer probe with 100% AT (Tm of 33° C.), that is, the equivalent electronic melting point (Em) at which dehybridization is 50% complete is higher for the 53% GC probe. Also, the fluorescent perturbation (FIGS. 1A and 1B, circled region) for the 10-mer probe with 53% GC is observed to be significantly different from that associated with the 100% AT probe.

Figure 2A:
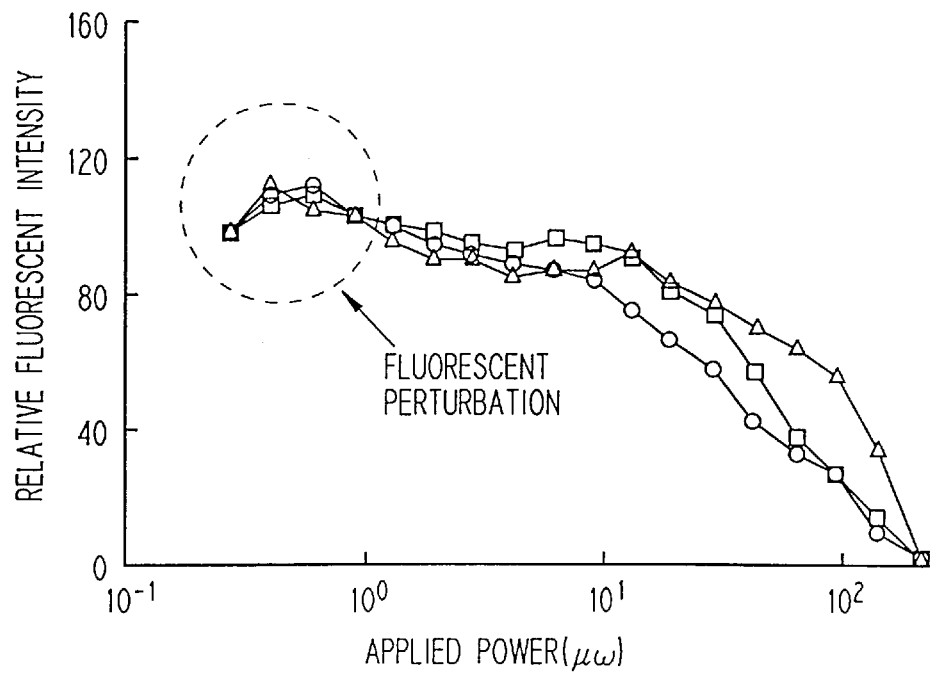
FIG. 2A is a graph of the relative fluorescent intensity verus applied power (microwatts) for a 20-mer oligomer duplex (100% AT).
Figure 2B:
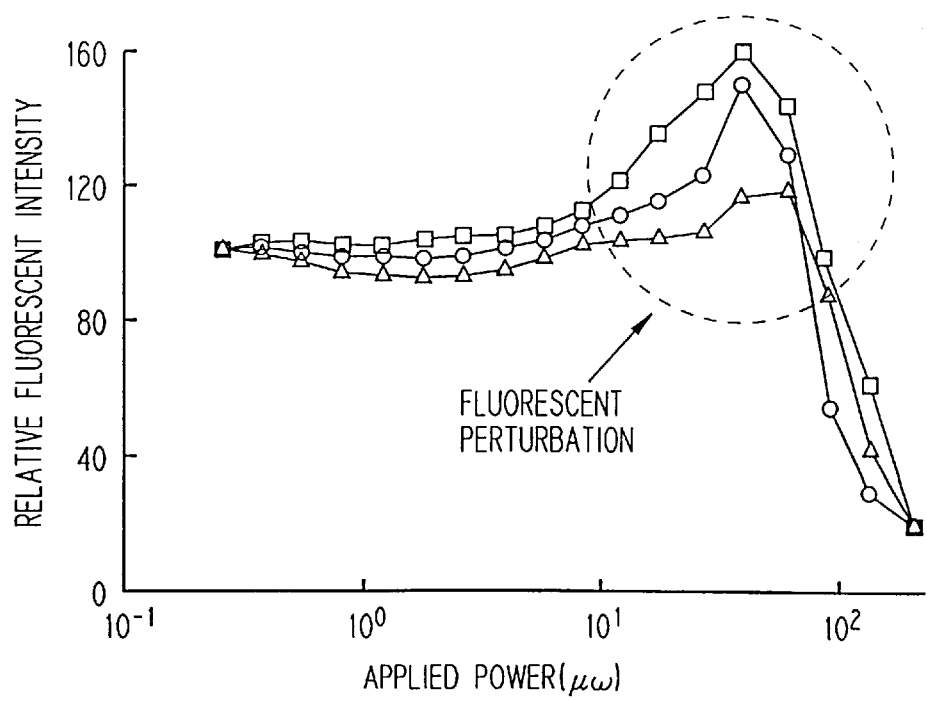
FIG. 2B is a plot of the relative fluorescent intensity verus applied power (microwatts) for a 19-mer oligomer duplex (53% GC).

FIGS. 2A and 2B show the results of denaturation experiments run on the APEX chip having 25 test microlocations with 20 micron deep wells to the underlying platinum electrodes. The well structures on the chip were filled with avidin/agarose composite, forming a 20 micron deep permeation layer. The same fluorescent target probes, capture probes and protocols were used in the deep well experiments as in the operation of the device resulting in the information of FIGS. 1A and 1B. As in the first experiments, the overall power ($\mu$W) necessary to dehybridize the 19-mer probe with 53% GC (Tm of 54° C.), is higher than for the 20-mer probe with 100% AT (Tm of 33° C.). Also, the slope for the 100% AT probe is much shallower, then for the 53% GC probe. The fluorescent perturbation/spike phenomena is very pronounced for the 19-mer probe with 53% GC in the deep well experiments.

The fluorescent perturbation phenomena correlates well with the sequence specificity of the dehybridization process. The power level ($\mu$W) value, amplitude and slope of the fluorescent spike are useful for many aspects of hybridization analysis including single base mismatch analysis. The fluorescent perturbation (Fp) value, namely those values associated with the fluorescence perturbation, e.g., onset value, peak height and slope, combined with the electronic melting (Em) values, namely, the half-height value of fluorescence, provide significantly higher reliability and additional certainty to hybridization match/mismatch analysis. By combining two or more analytical measurements, a more effective and precise determination may be made.

In the above experiments, the target probes were labeled with a Bodipy Texas Red fluorophore in their 5' terminal positions. While Bodipy TR is not a particularly environmentally sensitive fluorophore it nevertheless showed pronounced effects during electronic denaturation. More environmentally sensitive fluorophores may be used to obtain larger perturbations in their fluorescent properties during electronic dehybridization.

Figure 3A:
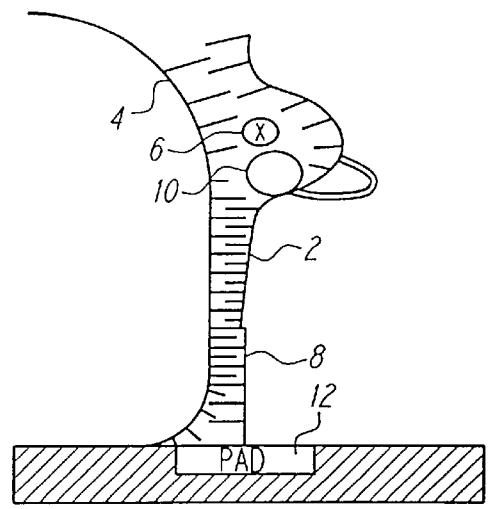
FIG. 3A shows a cross-sectional view of a mismatched test site having a capture probe, target DNA and a reporter probe.
Figure 4A:
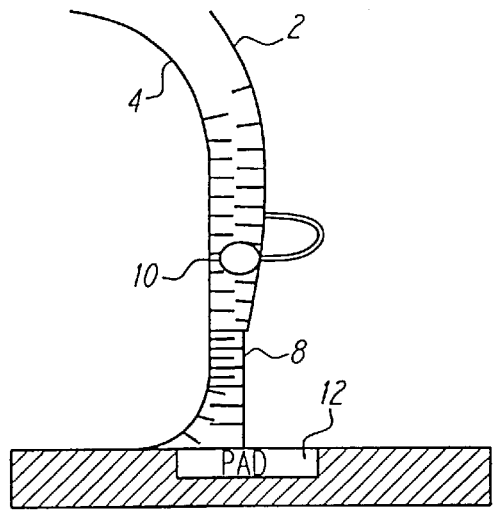
FIG. 4A is a cross-sectional view of a matched test site having a capture probe, target DNA and a reporter probe with an intercalated fluorophore.

The placement of a sensitive fluorescent label in optimal proximity to the initial denaturation site is preferred. By associating certain fluorescent labels in proximity to the denaturation site, as opposed to labeling at the end of the target or probe, increased specificity and enhanced effects may result. As shown in FIGS. 3A and 4A, an intercalating fluorophore 10 may be disposed between a reporter probe 2 and target DNA 4. FIG. 3A shows the condition in which the reporter probe 2 is mismatched from the target DNA 4 by a mismatched base 6. In each of FIGS. 3A and 4A, the capture probe 8 serves to capture the target DNA 4, with the pad 12 providing the electrophoretic action. Preferably, the intercalating fluorophore 10 would be placed next to the single base mismatch site 6 (FIG. 3A). The intercalating type fluorescent label could be, for example, ethidium bromide and acridine derivatives, or any other known fluorescent labels consistent with the objects of this device and its use.

Figure 3B:
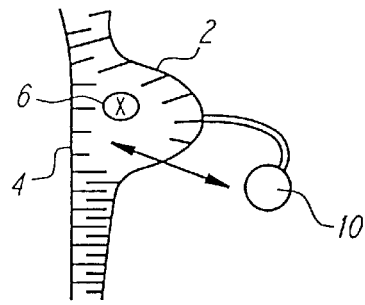
FIG. 3B is a cross-sectional view of target DNA and a reporter probe with an associated fluorophore.
Figure 4B:
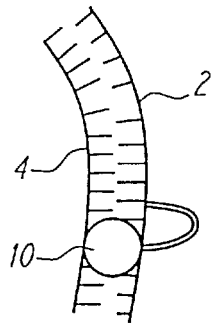
FIG. 4B is a cross-sectional view of target DNA and a reporter probe with an intercalating fluorophore.

FIGS. 3B and 4B show the condition of the reporter probe 2, the target DNA 4 and the mismatch base site 6 after the application of a pulse at the fluorescent perturbation value via the pad 12. The change from intercalated to the non-intercalated environment would produce a major change in fluorescent signal intensity for certain labels like ethidium.

Figure 3C:
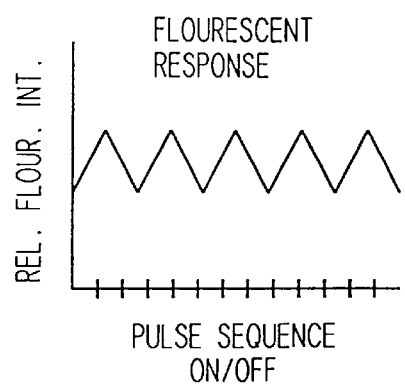
FIG. 3C is a graph of the fluorescent response graphing the relative fluorescent intensity as a function of time for a pulses sequence.
Figure 4C:
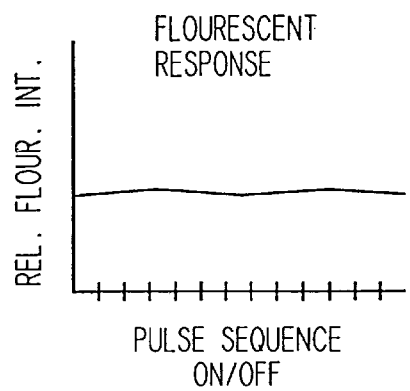
FIG. 4C is a graph of the fluorescent response showing the relative fluorescence intensity as a function of time for a pulsed sequence.

Furthermore, the use of a mismatch site directed fluorophore label does not require that the hybrid be completely denatured during the process. As shown in FIG. 3C and FIG. 4C, an analysis procedure is preferred in which an appropriate pulsed "Fp" power level is applied which causes a mismatched hybridization site to partially denature and renature relative to a matched hybridization site. The procedure results in an oscillating fluorescent signal being observed for mismatch hybrid site, while the fluorescent signal for the matched hybrid site remains unchanged. FIGS. 3C and 4C shows the relative fluorescent intensity as a function of varied applied power. This procedure provides a highly specific and discriminating method for single base mismatch analysis. Additional advantages include: (1) longer probes (>20-mer) than those used in conventional hybridization procedures can be used in this process, (2) Probe specificity is more determined by placement of the fluorescent label (particularly for single base mismatches), and (3) as the procedure does not require complete denaturation of the hybrid structures, each sample can be analyzed repetitively for providing a higher statistical significant data, such as through standard averaging techniques.

Figure 5:
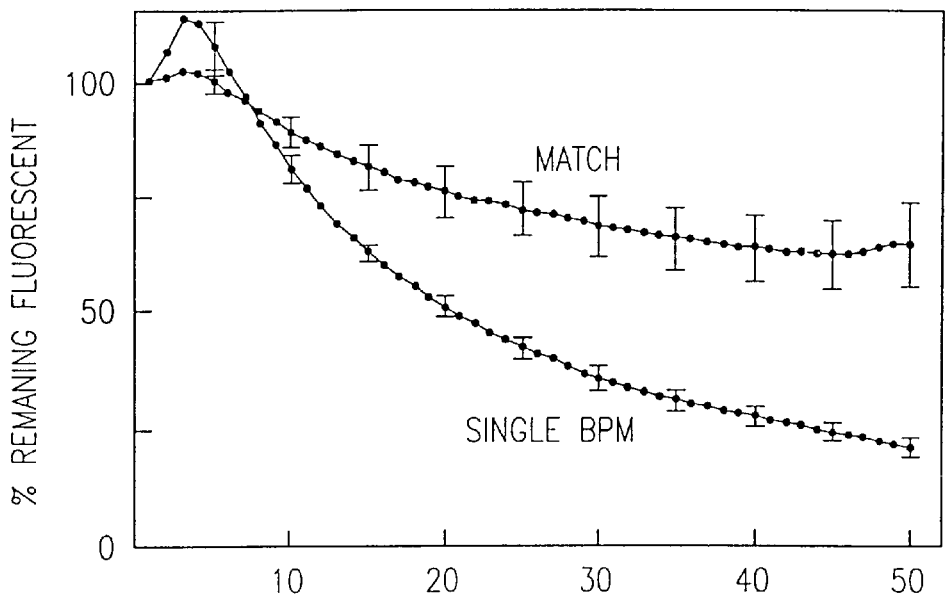
FIG. 5 shows the fluorescent intensity (% remaining Fluorescein) profiles as a function of time (seconds) for a one base mismatch and a match sequence for Ras G 22 mers during the basic electronic dehybridization process.

Referring to FIG. 5, in the process of carrying out electronic DNA hybridization and selective dehybridization (by electronic stringency) on active DNA chip devices (e.g., on an APEX chip), it was surprisingly discovered that the fluorescence signal from labeled reporter probes or target DNAs was perturbed during the initiation of electronic dehybridization at or around the electronic power levels (current and voltage) associated with that dehybridization process. Specifically, this fluorescence signal perturbation shows itself often as a rise or spike in the fluorescence intensity prior to dehybridization of the fluorescent labeled probe sequence from the DNA sequence attached to the microscopic test site (microlocation) on the DNA chip surface. The main region of fluorescence perturbation is shown in the dashed circle.

The fluorescent perturbation effect (FPE) is usually most pronounced for a one base mismatched probe sequence relative to the match probe sequence. In the general electronic hybridization and dehybridization procedure, the precisely controlled electronic stringency process results in a significant differential between the final fluorescent intensity values for the match versus the mismatch sequence. The mismatch sequence is more effectively dehybridized and more rapidly removed from the test location than the match sequence. In the general electronic hybridization and dehybridization process this difference in fluorescent intensity values is used to determine a discrimination ratio, which confirms and identifies that a particular mismatch was present in the sample. The particular parameters of electric field strength (current/voltage), solution conductivity, electrode geometry and pulsing time used to produce this selective dehybridization between the match and the mismatch occur at what is called the electronic melting temperature (Etm). The electronic dehybridization and stringency process allows match/mismatch discriminations to be carried out very rapidly (within substantially 20 to 60 seconds), compared with the classical hybridization stringency process, which involves temperature control and stringent washing procedures, which can take hours to complete. The single base pair mismatch (single BPM) sequence is observed to decrease faster than the match sequence allowing one to obtain a match/mismatch discrimination ratio for the pair.

Initial observations of the fluorescent perturbation effect (FPE), which occurs almost immediately upon initiation of the electronic dehybridization process, indicated that it was possible to use the FPE as a way to distinguish match/mismatched DNA hybrids even more rapidly, typically in less than a minute, and most preferably in several seconds or less. Another very powerful and novel feature of the FPE is that this technique does not require the removal of the probe or target sequence in order to discriminate a match from the mismatch hybrid, whereas the general electronic dehybridization process and classical hybridization techniques typically require the removal of the mismatch sequence relative to the matched sequence. A further advantage of the FPE technique is that probes of any size can potentially be used for match/mismatch hybrid discriminations or other applications. Longer probes sequences can provide overall better hybridization stability and selectivity.

Further investigations of the fluorescent perturbation effect has revealed other aspects and advantages of this unique phenomena which include: (1) that the amplitude, frequency, and slope of this fluorescent signal can provide a powerful analytical tool for other types of DNA hybridization analysis, in addition to the near instantaneous discrimination of single base mismatched DNA; (2) that multiple probe systems, involving a quencher probe and fluorescent acceptor probe (and donor probes), can be used to further enhance the FPE technique; (3) that a variety of electronic pulsing sequences (DC and AC variations) can be developed which further improve and broaden the scope of FPE based analysis of DNA and other molecular structures; (4) that the electronic fluorescence perturbation mechanism could lead to DNA sequencing applications; (5) that new arrangements of fluorescent donor/acceptor/quencher groups could be created for improved energy transfer mechanisms and applications; and (6) that novel electronic catalytic mechanisms could be created. These are the subjects of this invention.

The basic fluorescent perturbation effect occurs generally upon the initiation of electronic denaturation of match and mismatch hybrid pairs. In the case of the Ras (ras oncogene) hybrids in FIG. 5, the mismatch nucleotide is located approximately in the middle of the probe sequence, and the fluorescent label (Bodipy Texas Red) is covalently attached to the terminal position of the oligonucleotide sequence, approximately 10 bases from the mismatched nucleotide (see Example 1, below). Upon initiation of dehybridization process the fluorophore responds to the changing environment of the dehybridizing DNA strands by brightening. Generally, most fluorophores are somewhat sensitive to their local physical, chemical, and thermal environments; and a number of fluorophores are found to be extremely sensitive to changes in their environment. Environmental parameters such as hydrophilicity, hydrophobicity, pH, electrostatic charge, and Van der Waals interactions, can cause changes in the fluorescent intensity (quantum yield), the excitation/emission spectrum, and/or the fluorescent life time. Many of these environmental parameters are believed to change due to some or all of: (1) the disruption of the double-stranded DNA structure; (2) the effect of a DC or AC electric field and/or the electrophoretic effects on the fluorophore itself; (3) the effect of a DC or AC electric field and/or the electrophoretic effects on the fluorophore/DNA structure, which has its own unique set of interactions that can depend upon base sequence (AT or GC rich areas), and whether the fluorophore is associated with a double or single-stranded form of the nucleic acid; and/or (3) changes in the local electrochemical environment. It does appear that initial destabilization of the double-stranded structure is most important to the process. This is because the effect on the mismatch is more pronounced than for the match, both of which are present in the same general environment.

It is believed that the subtle fluorophore/DNA structural interactions are also very important. This is the basis for DNA sequencing techniques disclosed herein.

Figure 6:
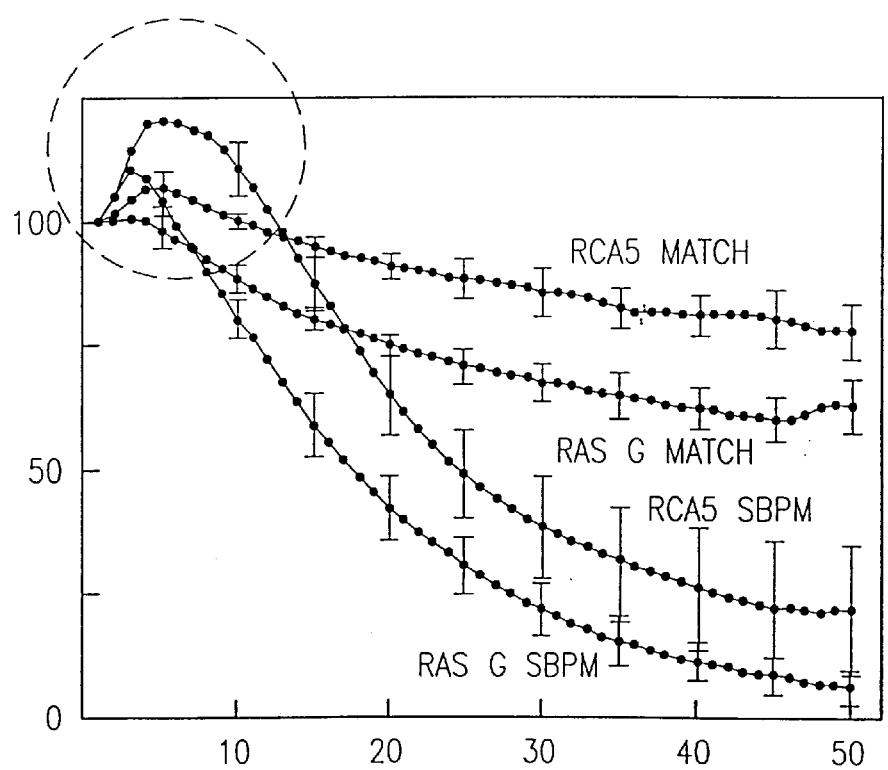
FIG. 6 shows the fluorescent intensity (% remaining fluorescence) as a function of time (seconds) observed during the general electronic dehybridization of match/mismatch hybrids for the Ras and RCA5 (HLA)systems.

FIG. 6 shows some further examples of the fluorescent perturbation effect observed during the general electronic dehybridization and stringency process for match/mismatch hybrids for the Ras and RCA5 (HLA) systems (see Example 2, below). The effect again is observed for both the Ras and RCA5 mismatch sequences, being particularly pronounced for RCA5 hybrid pair.

In general electronic hybridization and stringency experiments, the reporter or target probes are typically labeled with a Bodipy Texas Red fluorophore in their 5' (or 3')terminal positions. While Bodipy TR is not a particularly environmentally sensitive fluorophore it nevertheless showed pronounced effects during electronic dehybridization process. More environmentally sensitive fluorophores may be used to obtain larger perturbations in their fluorescent properties during FPE process. By way of example, these fluorophores and chromophores include: other Bodipy dye derivatives, ethidiums (in particular derivatized forms of ethidium dyes which can be covalently attached to DNA), or other intercalating fluorophores (which are or can be derivatized for attachment to DNA, acridines, fluoresceins, rhodoamines, Texas Red (sulforhodamine 101), Cy3 and Cy5 dyes, Lucifer Yellow, and Europium and Terbium chelate dye derivatives, IR144 and far red laser dyes and derivatives. Other fluorophores, chromophores and dyes consistent with the methods and objects of these inventions may be utilized.

In general, any dye which is sensitive to the environmental parameters such as hydrophilicity, hydrophobicity, pH, electrostatic charge, Van der Waals interactions, etc., that can cause changes in the fluorescent intensity (quantum yield), the excitation/emission spectrum, and/or the fluorescent life time, are potentially useful for FPE applications. More particularly useful, are those fluorophores, chromophores, or dyes which have properties which change or are perturbed due to the following.

(1) The initial disruption or destabilization of the double-stranded DNA structure. This is optionally just near the terminal position of the DNA structure where the fluorophore is located.

(2) The effects of the DC or AC electric field (or electrophoretic field) on the fluorophore itself. Of importance would be whether the fluorophore is neutral or charged, and whether the net charge is positive or negative. The net charge could strongly influence the perturbation effect, particularly if the fluorophore were positively charged. In this case, the fluorophore would tend to move in an opposite direction relative to the rest of the DNA molecule when an electric field is applied.

(3) The effect of the DC or AC electric field (or electrophoretic field) on the fluorophore/DNA interaction itself. Again, whether the fluorophore was neutral, net positive, or net negatively charged would have a pronounced effect on the nature and stability of the fluorophore/DNA interaction.

(4) The general spectral properties and robustness of the dye are also important. For example, the excitation and emission maxima, the Stokes shift, and the resistance to fading under excitation conditions are also important. Of particular usefulness would be those dyes which have excitation maxima at or above 480 nm, and emissions at or above 520 nm, and Stokes shifts of more than 20 nm. More useful, would be those dyes which have excitation maxima at or above 590 nm, and emissions at or above 620 nm, and Stokes shifts of more than 20 nm. Most useful, would be those dyes which have excitation maximum at or above 650 nm, and emissions at or above 670 nm, and Stokes shifts of more than 20 nm.

The placement of a sensitive fluorophore or chromophore label or reporter in optimal proximity to the initial destabilization or base mismatch site is important for achieving the electronic fluorescent perturbation effect (FPE). The preferred arrangements would be to have the fluorophore or chromophore within 0 to 10 bases of the initial destabilization or base mismatch site. The most preferred arrangements would be to have the fluorophore or chromophore within 0 to 5 bases of the initial destabilization or base mismatch site.

It should be kept in mind, that when a fluorophore or chromophore group is at the terminal position (5' or 3') of a DNA sequence which is hybridized to a complementary sequence, the group is already located in some sense at a "destabilized" site relative to the rest of the hybridized structure. This is because the terminal or end positions of a hybrid structure are less stable (the strands are opening and closing or fraying) relative to the internal hybridized sequence. One important aspect of this invention is to design the probe sequences such that they now position the further destabilizing base mismatch nucleotide site (in the target or probe sequence), so that upon hybridization the base mismatch is in closer proximity to the terminal fluorophore or chromophore group or groups. By associating the destabilization site in closer proximity to the terminal fluorophore or chromophore group(s), it is possible to utilize electronic pulsing sequences which produce fluorescent perturbation effects which correlate well with molecular structure, i.e., detect and identify point mutations, base deletions, base insertion, nucleotide repeat units, and other features important to DNA analysis.

Additional advantages to the FPE technique include: (1) the ability to utilize longer probes (>20-mer) than those used in conventional hybridization procedures, (2) that probe specificity can be determined by placement of the fluorophore or chromophore label (particularly for single base mismatches), and (3) FPE technique does not require dehybridization or removal of the mismatched probe sequence from the system; therefore, each sample can be analyzed repetitively providing a higher statistical significant to data, such as through signal averaging techniques.

Most particularly, this invention relates to using precisely controlled AC or DC electric fields or electrophoretic fields to affect or influence fluorophore or chromophore groups in special arrangements with molecular structures (such as nucleic acids), to produce rapid signal variations (perturbations) which correlate with and identify small differences in these molecular structures.

Most broadly, this invention relates to integrated microelectronic systems, devices, components, electronic based procedures, electronic based methods, electronic base mechanisms, and fluorophore/chromophore arrangements for: (1) molecular biological and clinical diagnostic analyses; (2) nucleic acid sequencing applications; and (3) for carrying out catalysis of biomolecular, organic, and inorganic reactions.

More specifically, the molecular biological and clinical diagnostic analyses relate to the utilization of the electronic fluorescent perturbation based mechanisms for the detection and identification of nucleic acid hybrids, single base mismatches, point mutations, single nucleotide polymorphisms (SNPs), base deletions, base insertions, crossover/splicing points (translocations), intron/exon junctions, restriction fragment length polymorphisms (RFLPs), short tandem repeats (STRs) and other repeating or polymorphic sequences in nucleic acid acids.

More specifically, the nucleic acid sequencing applications involve utilization of the electronic fluorescent perturbation based mechanisms to elucidate base sequence information in DNA, RNA, and in nucleic acid derivatives. Most particularly, to elucidate sequence information from the terminal ends of the nucleic acid molecules.

More specifically, the catalytic reactions relate to the utilization of electronic based catalytic mechanisms for carrying out biomolecular, biopolymer, organic polymer, inorganic polymer, organic, inorganic, and other types of chemical reactions. Additionally, the electronic based catalytic mechanisms can be utilized for carrying out nanofabrication, and other self-assembly or self-organizational processes.

More generally, the present invention relates to the design, fabrication, and uses of self-addressable self-assembling microelectronic integrated systems, devices, and components which utilize the electronic mechanisms for carrying out the controlled multi-step processing and multiplex reactions in a microscopic, semi-microscopic and macroscopic formats. These reactions include, but are not limited to, most molecular biological procedures, such as: (1) multiplex nucleic acid hybridization analysis in reverse dot blot formats, sandwich formats, homogeneous/heterogeneous formats, target/probe formats, and in-situ formats, and flow cytometry formats; (2) nucleic acid, DNA, and RNA sequencing; (3) molecular biological restriction reactions, ligation reactions, and amplification type reactions; (4) immunodiagnostic and antibody/antigen reactions; (5) cell typing and separation procedures; and (6) enzymatic and clinical chemistry type reactions and assays.

In addition, the integrated systems, devices, and components which utilize electronic based catalytic mechanisms are able to carry out biomolecular, biopolymer and other types of chemical reactions: (1) based on electric field catalysis; and/or (2) based on multi-step combinatorial biopolymer synthesis, including, but not limited to, the synthesis of polynucleotides and oligonucleotides, peptides, organic molecules, biopolymers, organic polymers, mixed biopolymers/organic polymers, two and three dimensional nanostructures, and nanostructures and micron-scale structures on or within silicon or other substrate materials.

Additionally, with respect to electronic fluorescent perturbation mechanisms, the present invention relates to unique intermolecular and intramolecular constructs and arrangements of chromophores, fluorophores, luminescent molecules or moities, metal chelates (complexes), enzymes, peptides, and amino acids, associated with nucleic acid sequences, polypeptide sequences, and/or other polymeric materials. Of particular importance being those constructs and arrangements of fluorphores and chromophores which produce fluorescent energy transfer, charge transfer or mechanical mechanisms which can be modulated or affected by the AC or DC electric fields or electrophoretic fields to produce fluorescent or luminescent signals which provide information about molecular structure.

With respect to the electronic catalytic mechanisms in homogeneous (solution) or heterogeneous (solution/solid support) formats, the present invention relates to unique intermolecular and intramolecular constructs and arrangements of chromophores, fluorophores, luminescent molecules or moities, metal chelates (complexes), enzymes, peptides, and amino acids, nucleophilic molecules or moities, electrophilic molecules or moities, general acid or base catalytic molecules or moieties, and substrate binding site molecules and moities, associated with nucleic acid sequences, polypeptide sequences, other biopolymers, organic polymers, inorganic polymers, and other polymeric materials.

Additionally, this invention relates to the utilization of electric or electrophoretic fields to induce fluorescent perturbation based mechanisms in arrangements of fluorophores and chromophores in solid state or sol-gel state optoelectronic devices and optical memory materials.

FPE With A Single Fluorophore

Figure 7A:
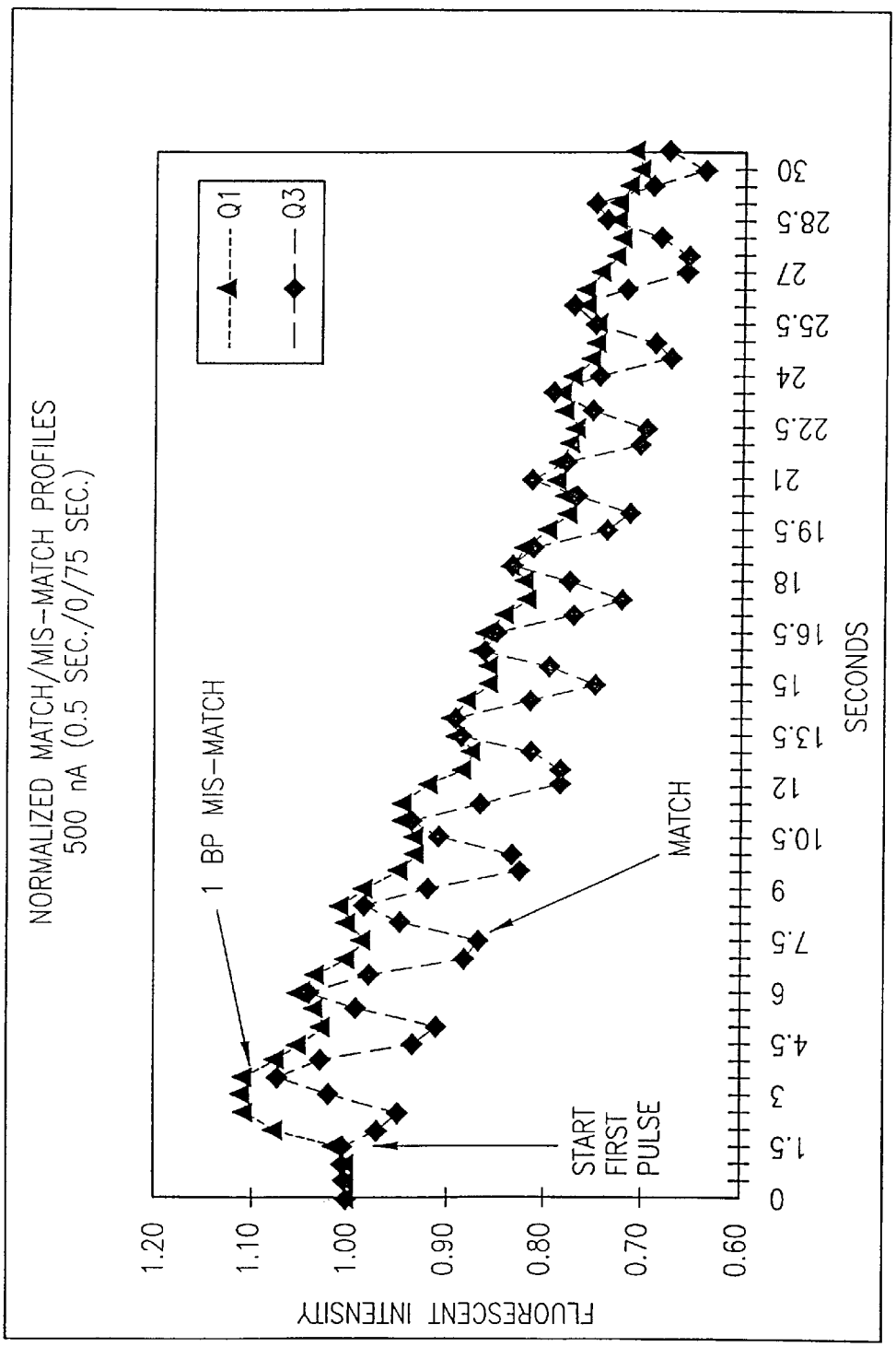
FIG. 7A shows a graph of the normalized fluorescent intensity versus time (seconds) for match/mismatch profiles exhibiting the oscillating fluorescent perturbation effect.

FIG. 7A shows a graph of the normalized match/mismatch profiles exhibiting the oscillating fluorescent perturbation effect for a probe with a single fluorescent reporter group. A pronounced difference is observed between the match and the mismatch hybrids. The match and mismatch hybrid pairs have the mismatched nucleotide located two bases from the Bodipy Texas Red fluorescent reporter group which is attached to the 3'-terminal position of the reporter probe. The x-axis of the graph is seconds, and the y-axis is relative fluorescent intensity units. The electronic pulse sequence used was 500 nA for 0.5 seconds on/0.75 second off, run for 30 seconds (see Example 3). In this example the match and mismatch hybrid pairs have the mismatched nucleotide located two bases from the Bodipy Texas Red fluorescent reporter group which is attached to the 3'-terminal position of the reporter probe.

Figure 7B:
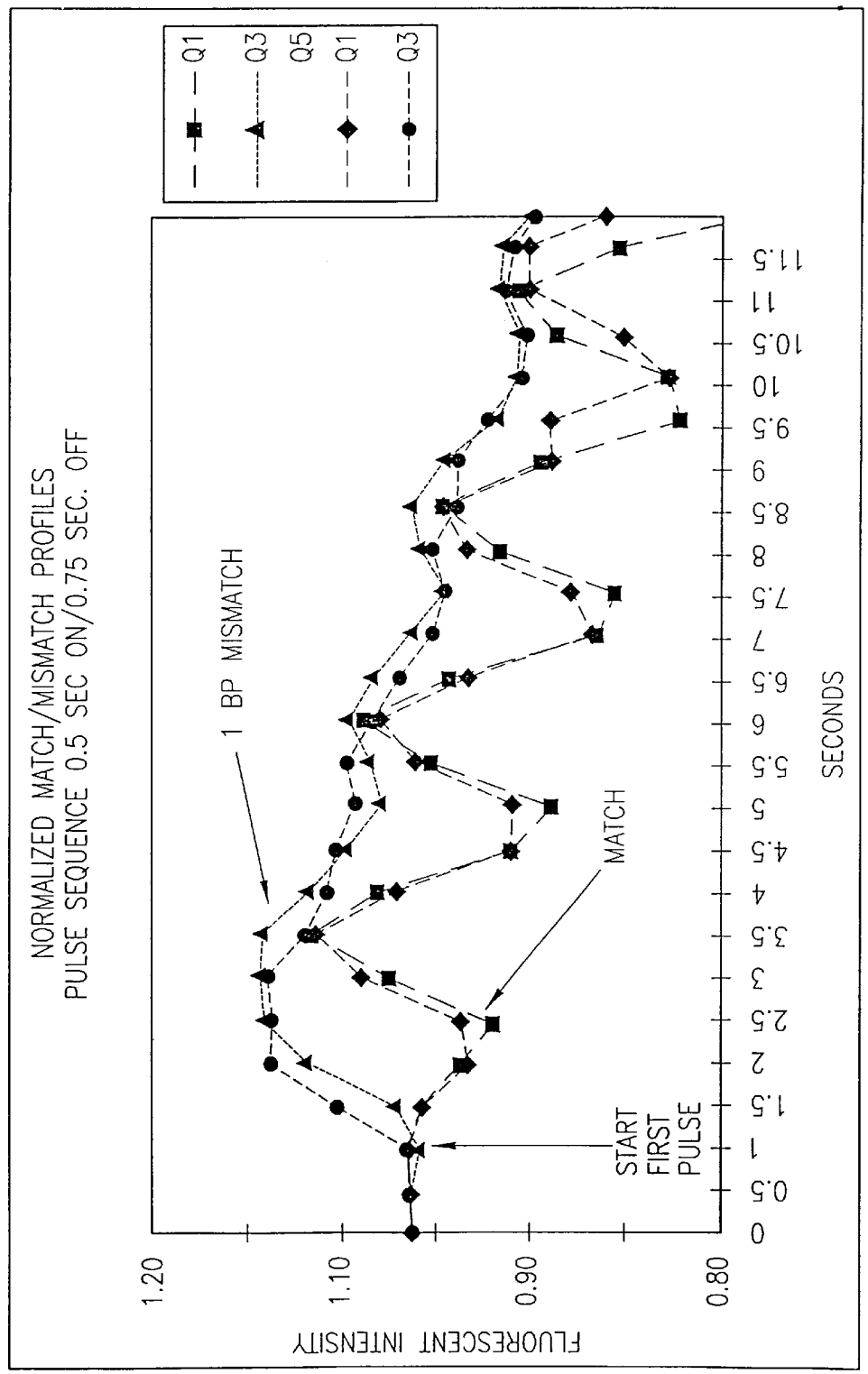
FIG. 7B shows an expanded view graph of the first 12 seconds of the graph of FIG. 7A.

FIG. 7B now shows an expanded view graph of the first 12 seconds for the normalized match/mismatch profiles exhibiting the oscillating fluorescent perturbation effect. A very pronounced difference is observed in the first few seconds after the pulse sequence is initiated, after which the match and the mismatch continue to oscillate at different amplitudes. It is believed that the higher amplitude oscillation by the match is due to the faster and more efficient rehybridization by the fully complementary (match) sequence relative to a non-fully complementary sequence (mismatch). This faster "snap-back" of the match relative to the mismatch may be used to distinguish those cases. FIG. 7B shows that the upon initiation of the DC pulse sequence that the fluorescent intensity for the mismatch rises rapidly, while the fluorescent intensity for the match actually decreases momentarily. The mismatch and the match then seem to come into phase, but oscillate at different amplitudes. It is such pronounced differences which allow the FPE to be used to differentiate between the match and mismatched DNA structures.

Figure 8B:
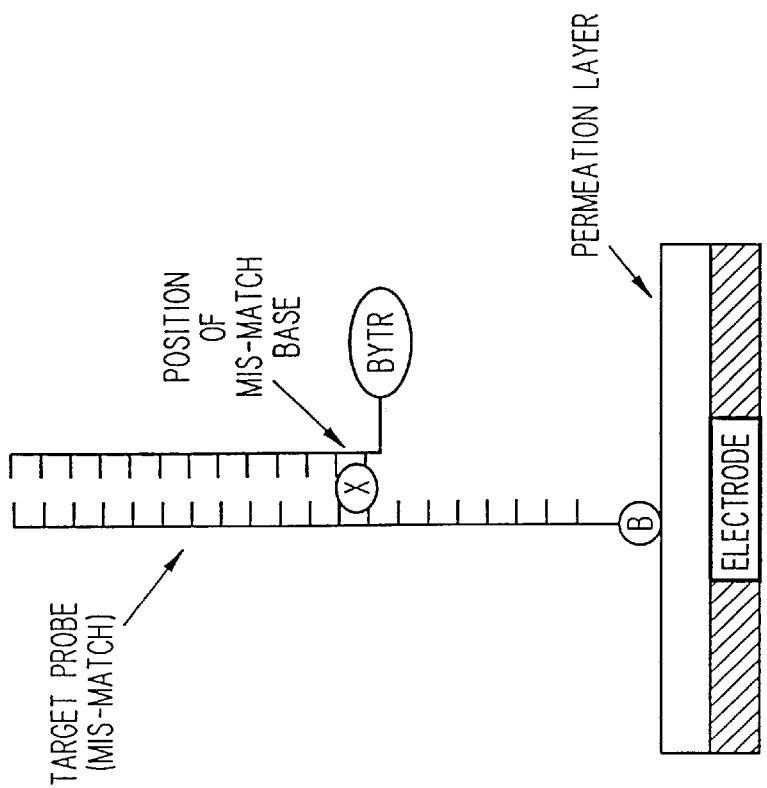
FIG. 8B shows a schematic representation of FIG. 8A, but where a mismatch between the target and probe is present.
Figure 8A:
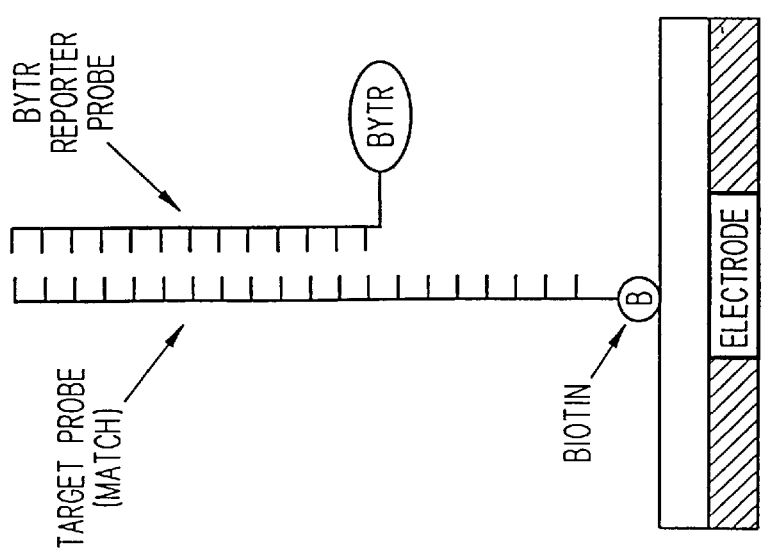
FIG. 8A shows a schematic representation for the hybridized arrangement of the target probe and the Bodipy Texas Red labeled reporter probe, and the position of the one base mismatch.

FIGS. 8A and 8B show a schematic representation for the hybridized arrangement of the target probe and the Bodipy Texas Red labeled reporter probe, and the position of the one base mismatch (FIG. 8B). The mismatched nucleotide is located two bases from the Bodipy Texas Red fluorescent reporter group which is attached to the 3'-terminal position of the reporter probe. The most preferred arrangements for carrying out FPE techniques with a single fluorophore would be to have it located within 0 to 5 bases of the mismatched location (see Example 3, below).

FPE With Multiple Fluorophore/Chromophore Arrangements

Figure 9:
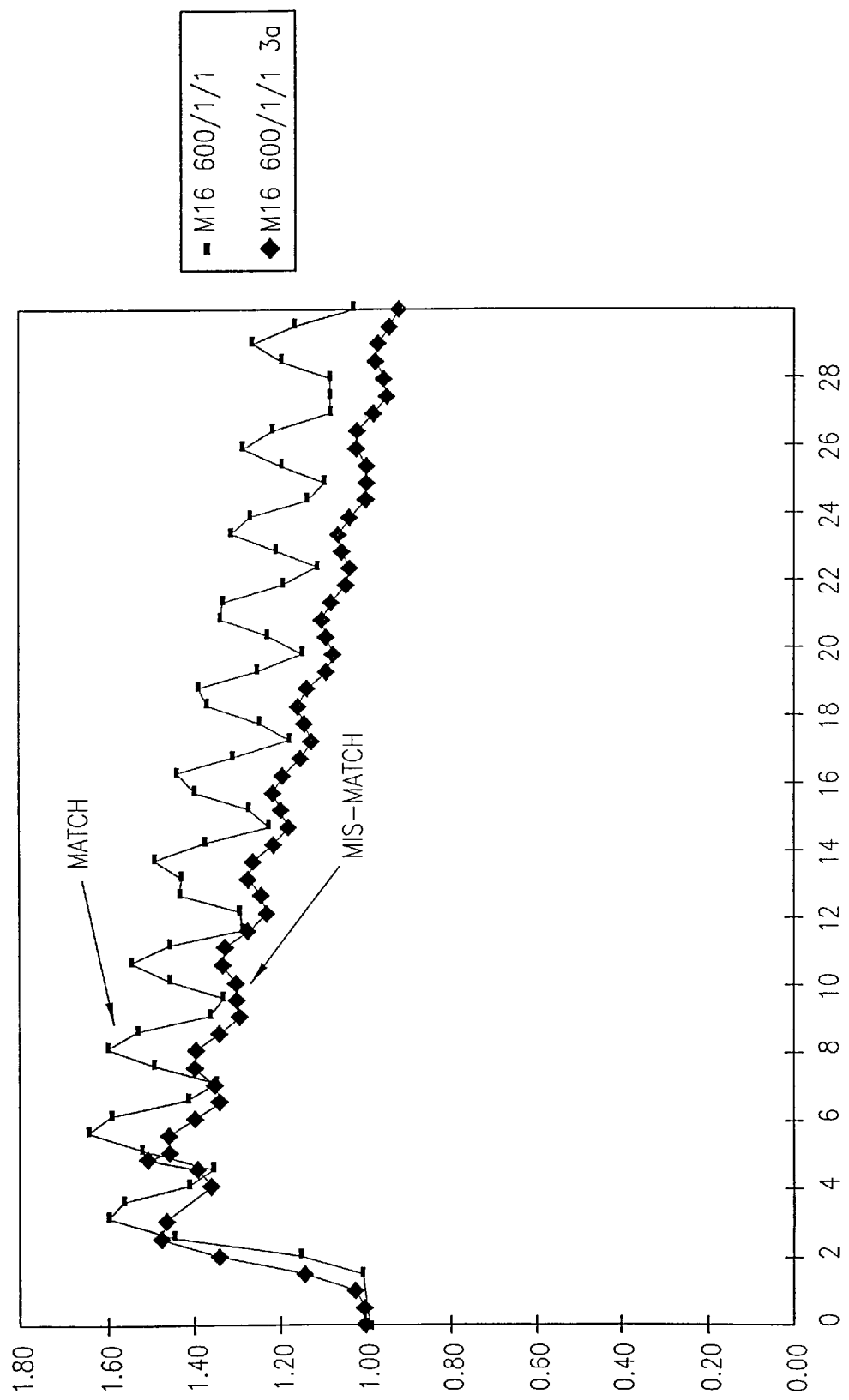
FIG. 9 shows a graph of the normalized fluorescent intensity as a function of time (seconds) match/mismatch profiles exhibiting the oscillating fluorescent perturbation effect, in the presence of a second probe containing a quencher group (Malachite Green).

FIG. 9 shows a graph of the normalized match/mismatch profiles exhibiting the oscillating fluorescent perturbation effect, in the presence of a second probe containing a quencher group (Malachite Green). A pronounced difference is observed between the match and the mismatch hybrids upon application of the electric field. There is immediately a very large increase in fluorescent intensity due to the loss of the quenching effect upon initiation of the electric field. After the "de-quenching" the match and the mismatch continue to oscillate at different amplitudes. This represent just one example of how a unique fluorophore/chromophore arrangement can be used to enhance or improve the FPE technique. Additionally, this represents an example of how a unique energy transfer or quenching mechanism can be designed, which responds to a DC pulsing electric field (electrophoretic field), and produces a unique fluorescent response (a dramatic increase in intensity). It is also disclosed in this invention, that AC electric fields (including high frequencies >100 Hz), would have fluorescent perturbation effects which would be useful for analysis of molecular structures, in particular for DNA hybridization analysis.

In the example shown in FIG. 9, the match and mismatch hybrid pairs have the mismatched nucleotide located two bases from the Bodipy Texas Red fluorescent reporter group, which is attached to the 3'-terminal position of the reporter probe. The second probe (quencher probe) hybridizes to the target sequence in such a way that it positions the Malachite Green quencher group (attached at the 5'-terminal position) within three bases of the Bodipy Texas Red fluorophore group on the 3'-terminal position of the reporter probe. Upon hybridization, the quencher probe causes about a 40–50% decrease in the fluorescent intensity of the Bodipy Texas Red reporter (which is eliminated when the electric field is applied). Other arrangements and quencher chromophores could produce even better quenching and reduction of fluorescence from the reporter group. In FIG. 9, the x-axis of the graph is in seconds, and the y-axis is in relative fluorescent intensity units. The electronic pulse sequence used was 600 nA for 1.0 seconds on/1.5 second off, run for 30 seconds (see Example 4, below).

Figure 10B:
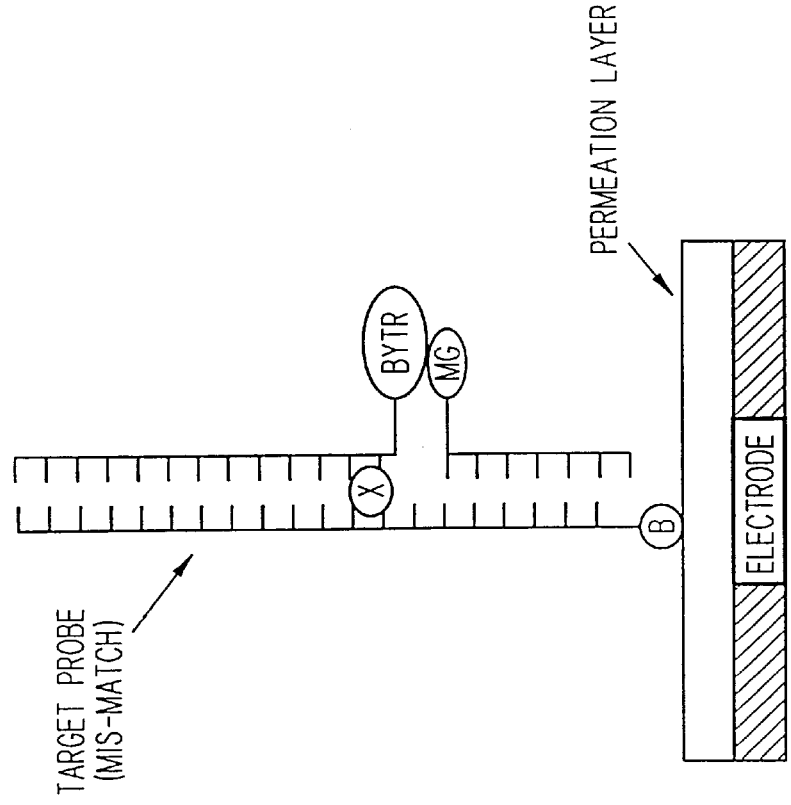
FIG. 10B shows the schematic representation of FIG. 10A with a mismatch between the target and the probe.
Figure 10A:
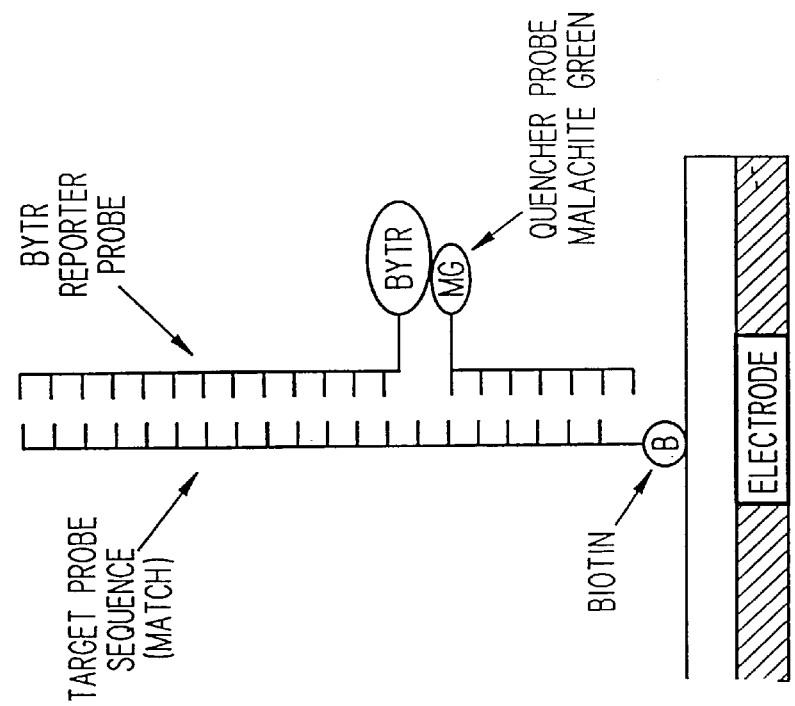
FIG. 10A shows a schematic representation for the hybridized arrangement of the target probe, the Bodipy Texas Red labeled reporter probe, and the Malachite Green quencher probe.

FIGS. 10A and 10B show a schematic representation for the hybridized arrangement of the target probe, the Bodipy Texas Red labeled reporter probe, and the Malachite Green quencher probe. The mismatched nucleotide (FIG. 10B) is located two bases from the fluorescent reporter group (Bodipy Texas Red) located on the terminal position of the reporter probe. The second probe (quencher probe) hybridizes to the target sequence in such a way that it positions the Malachite Green quencher group (attached at the 5'-terminal position) within three bases of the Bodipy Texas Red fluorophore group on the 3'-terminal position of the reporter probe. Other useful fluorophore/chromophore forms and arrangements would include those in which the quencher probe is designed to be hybridized within 0 to 5 bases of the mismatch position.

Of particular usefulness for this invention is one of the preferred arrangement shown in FIGS. 11A and 11B. In this example, the first probe (a capture/quencher probe sequence) has two terminal functional groups, a 5'-terminal biotin group which allows the probe to be immobilized to the surface (permeation layer) of a microlocation test site on an active DNA chip or other hybridzation device. The second functional group being a quencher group, (such as Malachite Green, Reactive Red, or other quencher chromophore), which is at the 3'-terminal position of the capture/quencher probe. The capture/quencher probes are made complementary to the match and mismatch point mutation sequences of interest. These probes allow the target DNA (RNA) sequence to be captured by selective hybridization and immobilized on the microlocation test site. The sequence is designed to optimally position the (potential) mismatched nucleotide within one to five bases of the quencher group. After the hybridization/capture of the target DNA (RNA) sequence, the second probe (acceptor reporter) is added and hybridized to the immobilized target DNA/quencher probe. The acceptor/reporter probe is labeled in its 5'-termininal position with a suitable fluorophore (Bodipy Texas Red, or other reporter group), and designed to hybridize to the target DNA sequence in such a away as to be optimally positioned within 1 to 5 bases of the quencher group, where upon hybridization the acceptor reporter groups fluorescence is quenched. Upon application of the appropriate electronic DC pulsing sequence (current/on time/off time) an electric field is induced which causes the match and mismatched hybrids to produce a fluorescent perturbation effect and oscillations which allow them to be distinguished and identified. It should be pointed out that the above hybridization procedure could also be carried out in a semi-homogeneous format, in which the target DNA sequence is first hybridized in solution with the reporter probe sequence, before hybridization to the immobilized capture/quencher probe. The above describes just some of the potentially useful formats for PFE. It is important to realize that flexibility in choosing various FPE techniques and formats will be advantageous for successful broad area hybridization diagnostics. The scope of this invention also includes the utilization of the FPE processes described above, in highly multipexed formats on APEX DNA chips and array devices.

Additionally, the scope of this invention includes the use and incorporation of various donor/acceptor/quencher, mechanisms, probe arrangements and hybridization formats which were described in our photonic patents (U.S. Pat. No. 5,532,129 and U.S. Pat. No. 5,565,322) and optical memory application (WO 95/34890). The novel electronic pulsing scenarios combined with the donor/acceptor/quencher arrangements described in the above applications leads to useful FPE quenching and energy transfer mechanism, which further enhance and expand the usefulness of the techniques for DNA hybridization and other molecular analysis.

Electronic Perturbation Catalysis

The discovery of the fluorescent perturbation effect has also contributed to the further discovery of a way to carry out novel electronic perturbation catalysis. In particular it lead to discovering a way to over come what is called the leaving group effect in enzyme catalysis. Investigators trying to create synthetic enzyme-like catalysts have not been able to overcome this obstacle. (See M. J. Heller, J. A. Walder, and I. M. Klotz, Intramolecular Catalysis of Acylation and Deacylation in Peptides Containing Cysteine and Histidine, J. American Chemical Society, 99, 2780, 1997).

Figure 12:
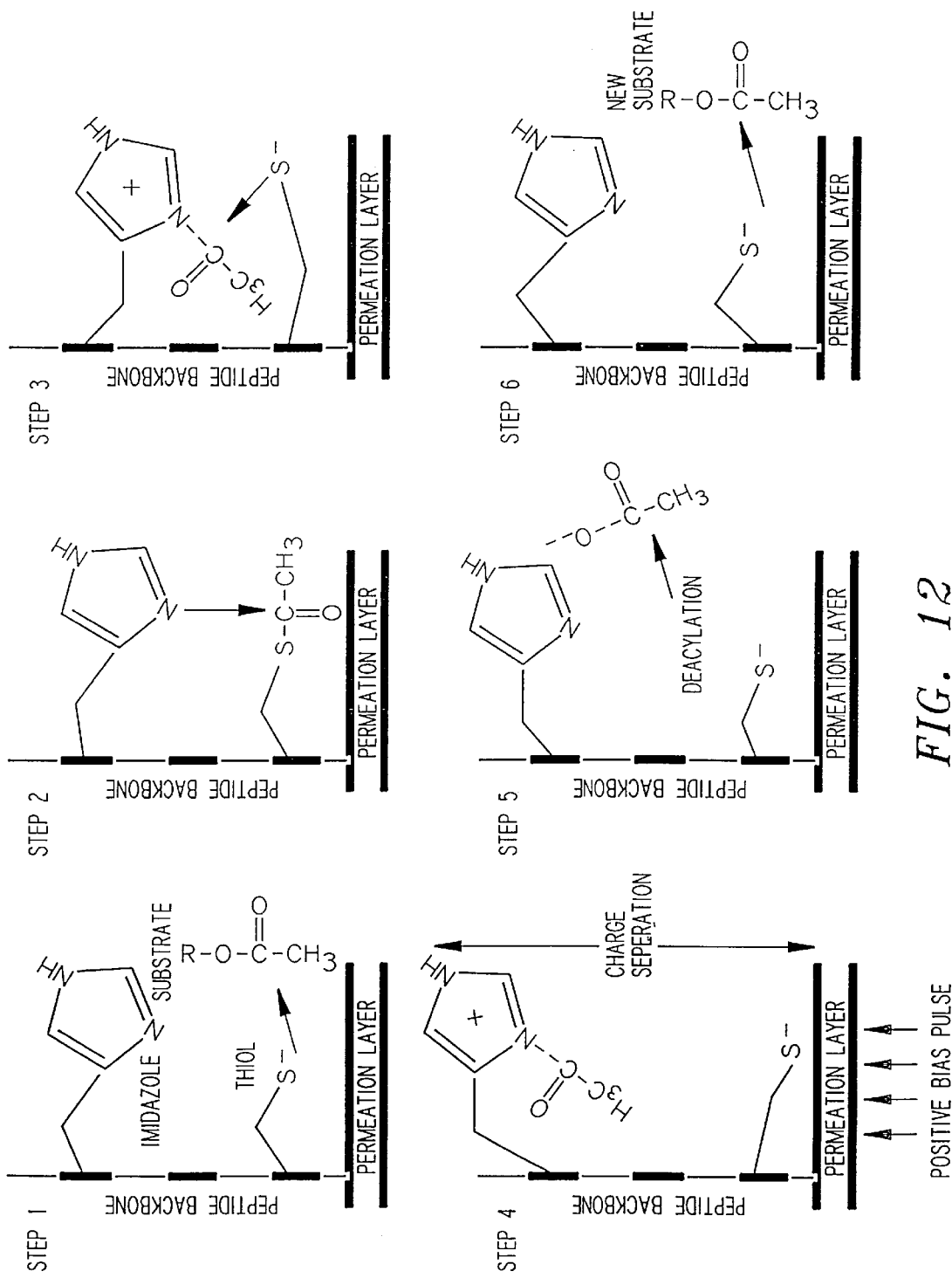
FIG. 12 shows a sequence of steps for electronic perturbation catalysis.

FIG. 12 shows a diagram of a peptide structure containing an arrangement of nucleophilic groups (cysteine-thiol and histidine-imidazole) designed to carry out electronic perturbation catalysis, ester hydrolysis and deacylation in particular. Two examples of such cysteine and histidine containing peptide structures include: Gly-His-Phe-Cys-Phe-Gly (SEQUENCE ID NO. 3) and Gly-His-Pro-Cys-Pro-Gly (SEQUENCE ID NO. 4). In the example shown in FIG. 12, a cysteine (thiol) and histidine (imidazole) containing catalytic peptide sequence is immobilized onto the surface (permeation layer) of a microlocation on an active electronic device (via the terminal alpha amino group). The system is designed to catalyze the cleavage of esters and amide bonds (Step 1). The catalytic peptide/device is exposed to a solution containing the particular substrate of interest (ester, amide, etc.), which hydrolyzes and forms an acyl-thiol intermediate (Steps 1 and 2). In general, the acyl-thiol group will not deacylate even when the imidazole group is in close proximity, because of the back attack between the two nucleophiles (Step 3). Electronic perturbation catalysis is carried out by applying an appropriate electronic pulsing sequence (current, on time/off time), which causes charge separation between the negatively charged thiol group and the positively charged acyl-imidazole group (Step 4), allowing the acyl-imidazole group to effectively deacylate before the thiol group can re-attack (Step 5). The system is now ready to catalyze the hydrolysis of a new substrate molecule (Step 6). This example represent just one of many possible catalytic arrangements and applications for electronic perturbation catalysis.

EXPERIMENTAL RESULTS

EXAMPLE 1

Ras G Match/Mismatch

APEX Chip Preparation and Capture Probe Loading— APEX active DNA chips, with 25 microlocation test sites (80 microns in diameter) were coated with streptavidin agarose accordingly. A 2.5% glyoxal agarose (FMC) solution in water was made according to manufacturer's instructions. The stock was equilibrated at 65° C., for 5 minutes. Chips were spin coated at 2.5K rpm for 20 seconds. Another layer was then applied at 10K rpm for 20 seconds. This second "thin layer" was composed of a 1:4 mix of 5 mg/ml streptavidin (BM) in 50 mM NaPhosphate, 250 mM NaCl and 2.5% glyoxal agarose.

The chips were baked at 37° C. for 30 minutes. Streptavidin was coupled to the agarose via Schiff's base reduction in 0.1M NaCNBH3 in 0.3M NaBorate, pH 9.0, for 60 minutes, at room temperature. The remaining aldehydes were capped with 0.1M glycine, for 30 minutes, at room temperature, and finally rinsed in water, dried under N2 and then stored at 4° C.

The table below gives the sequence and labeling positions for all the oligonucleotide probes and target sequences used in examples 1 and 2. Mismatches are underlined and bolded.

| Name | Sequence (5'—3') | | Modification | Modified end |
|---|---|---|---|---|
| Ras 411 | GCCCACACCGCCGGCGCCCACC | (SEQUENCE ID NO:5) | Bodipy Texas Red | 5' |
| Ras 415 | GGTGGGCGCCGGCGGTGTGGGC | (SEQUENCE ID NO:6) | Biotin | 5' |
| Ras 416 | GGTGGGCGCCGGAGGTGTGGGC | (SEQUENCE ID NO:7) | Biotin | 5' |

-continued

| Name | Sequence (5'-3') | | Modification | Modified end |
|---|---|---|---|---|
| HLA 253 | CCACGTAGAACTGCTCATC | (SEQUENCE ID NO:8) | Bodipy Texas Red | 5' |
| HLA 241 | GATGAGCAGTTCTACGTGG | (SEQUENCE ID NO:9) | Biotin | 3' |
| HLA 378 | GATGAGCAG<u>C</u>TCTACGTGG | (SEQUENCE ID NO:10) | Biotin | 3' |
| HLA 375 | <u>T</u>ATGAGCAGTTCTACGTGG | (SEQUENCE ID NO:11) | Biotin | 3' |
| HLA 376 | GATGAGCAGTTCTACGTG<u>T</u> | (SEQUENCE ID NO:12) | Biotin | 3' |
| HLA 401 | GATGAGCAGTTCTACGTGG | (SEQUENCE ID NO:13) | Biotin | 5' |

Capture Probe Addressing for Example 1—Columns 1 & 2 on the APEX chip were electronically addressed with the Ras 415 (match) sequence and columns 4 & 5 loaded with Ras 416 (mismatch) sequence. Addressing was carried out in 50 M cysteine, 1 μM oligonucleotide, 200 nA for 1 min. The target/reporter sequence Ras 411 was passively hybridized in 500 mM NaCl, 50 mM NaPhosphate pH 7.4, at room temperature for 5 minutes). Electronic dehybridization and stringency was done at 1.5 μA/microlocation, DC pulsing for 0.1 sec on, 0.2 sec off, 150 cycles (20 mM NaPhosphate, pH 7.4). Microlocations were given electronic stringency individually. Fluorescence signal was captured at 1 second intervals. Normalized displayed is the average of three test sites for each point. Error bars are standard deviations. Results are shown in FIG. 5.

EXAMPLE 2

Ras G and HLA Match/Mismatches

The APEX chip preparation procedure was the same as Example 1. Capture probe addressing conditions were the same as Example 1. The Ras 415 sequence was electronically addressed to all 5 microlocations in column 1 and Ras 416 addressed to all 5 microlocations in column 2 of the APEX chip. The HLA 241 sequence was addressed to all 5 microlocations in column 4 and HLA 378 was addressed to all 5 microlocations in column 5. The Ras 411 and HLA 253 fluorescent target probes were mixed and passively hybridized to the APEX chip. Electronic dehybridization and stringency was carried out for the Ras system at 1.5 μA/microlocation, DC pulsing for 0.1 sec on, 0.2 sec off, 150 cycles (20 mM NaPhosphate, pH 7.4). Electronic dehybridization and stringency for the HLA system was carried out at 0.6 μA/microlocation, DC pulsing for 0.1 sec on, 0.2 sec off, 150 cycles (20 mM NaPhosphate, pH 7.4). Data collected as reported above. FIG. 6 shows the results for Example 2.

EXAMPLE 3

Fluorescent Perturbation Effect With Single Fluorophore

APEX Chip Preparation and Capture Probe Loading—APEX active DNA chips, with 25 microlocation test sites (80 microns in diameter) were coated with streptavidin agarose accordingly. A 2.5% glyoxal agarose (FMC) solution in water was made according to manufacturer's instructions. The stock was equilibrated at 65° C., for 5 minutes. Chips were spin coated at 2.5K rpm for 20 seconds. Another layer was then applied at 10K rpm for 20 seconds. This second "thin layer" was composed of a 1:4 mix of mg/ml streptavidin (BM) in 50 mM NaPhosphate, 250 mM NaCl and 2.5% glyoxal agarose. The chips were baked at 37° C. for 30 minutes. Streptavidin was coupled to the agarose via Schiff's base reduction in 0.1M NaCNBH3 in 0.3M NaBorate, pH 9.0, for 60 minutes, at room temperature. The remaining aldehydes were capped with 0.1M glycine, for 30 minutes, at room temperature, and finally rinsed in water, dried under N2 and then stored at 4° C.

The sequences for the oligonucleotide reporter probe, quencher probe and capture probe used in Examples 3 and 4 are listed below:

```
QATAR-1 (perfect match for reporter and quencher)
5'-biotin-CAC gAg AgA CTC ATg AgC Agg ggC TAg CCg ATC ggg TCC TCA ggt    (SEQUENCE ID NO:14)
CAA gTC QATAR-2
5'-biotin-CAC gAg AgA CTC ATg AgC Agg (C)gC TAg CCg ATC ggg TCC TCA      (SEQUENCE ID NO:15)
ggT CAA gTC QATAR-3A (1 base mismatch)
5'-biotin-CAC gAg AgA CTC ATg AgC Agg ggC TAg CC(A) ATC ggg TCC TCA      (SEQUENCE ID NO:16)
ggT CAA gTC QATAR-4A (2 base mismatch)
5'-biotin-CAC gAg AgA CTC ATg AgC Agg ggC TAg CC(A) A(C)C ggg TCC TCA    (SEQUENCE ID NO:17)
ggT CAA gTC QATAR-5A (prefect match to reporter, no quencher hybridization)
5'-biotin-gCA CCT gAC TCC TgA ggA gAA gTC CCg ATC ggg TCC TCA ggT        (SEQUENCE ID NO:18)
CAA gTC
```

-continued

ET60-BODIPY TR (Reporter)
5'-TgA CCT gAg gAC CCg ATC g - BODIPY TR                    (SEQUENCE ID NO:19)

ET71-Malachite Green (Quencher)
5'-malachite green - Ag CCC CTg CTC ATg AgT CTC T           (SEQUENCE ID NO:20)

The capture probes were addressed to specific microlocation test sites (pads) on the APEX chip as follows: a 10 μl aliquot containing 500nM capture probe in 50 mM histidine buffer was applied to the chip and positive bias was applied at 200 nA/pad, for 30 seconds. The bias was turned off and the chip was fluidically washed in 50 mM histidine. QATAR-1 was addressed to column 1, QATAR-3A was addressed to column 2, QATAR-4A was addressed to column 3, and QATAR-5 was addressed to column 4.

Hybridization and Quenching Efficiency

The addressed APEX chips were passively hybridized with ET60-BTR reporter with/without ET71-MG quencher at 500 nM each in 100 mM NaPhosphate, at pH 7.2, 250 mM NaCl, at 65° C. in a heat block, for 2 minutes. The chips were washed in 20 mM NaPhosphate, pH 7.2, at room temperature, 3 times for 10 minutes each wash.

| Capture | Reporter ET60-BTR | Quencher ET71-MG |
|---------|-------------------|------------------|
| QATAR-1 | match | match |
| QATAR-3A | 1 base pair mismatch | match |
| QATAR-4A | 2 base pair mismatch | match |
| QATAR-5 | match | none |

Comparison of hybridization signal intensities indicated that fluorescent quenching was about 50% efficient. This could be improved with optimized spacing and or increased purification of the probes (higher specific activity).

Fluorescence Perturbation for Reporter Probe Only

The chips were mounted on a probe station with a probe card to provide electrical contact to the chip, waveforms were supplied by Keithley Power Supply, images acquired via Optronics cooled color CCD and NIH image software was used to analyze the data. The preferred imaging system is that disclosed in cop ending U.S. Application entitled "Scanning Optical Detection System", filed May 1, 1997, incorporated herein by reference as if fully set forth herein.

Chips were prepared and hybridized as described in Example 1 and 2. In 20 mM NaPhosophate, pH 7.2, individual pads were biased negative and a pulse waveform was applied. Parameters tested were pulse frequency, % duty cycle, and amplitude. Good fluorescence perturbation results were observed at 600 nA/1 sec On/1.5 sec Off. The camera integration was 1.0 second. Higher pulse frequencies could also be effective but these experiments were limited by the amount of fluorescence at each pad location which necessitated longer camera integration times.

Results from the perfect match reporter/quencher pair on QATAR 1 showed an approximately 10% increase in fluorescence intensity when the power was first applied and the intensity oscillated during the course of the waveform. On QATAR-5 "which " did not have the quencher hybridized) there was very little fluorescence perturbation. Both QATAR 3a and 4a exhibited some fluorescence perturbation but not as much as QATAR1. Additionally, signal loss after bias was greatest for QATAR-4A, followed by 3A, followed by 5 and then 1. This would be expected based on the hybrid Tm's. The results for QATAR-1 (match) and the QATAR-3 (mismatch) are shown in FIGS. 7A and 7B.

EXAMPLE 4

Fluorescence Perturbation With Reporter and Quencher Probes

APEX chips were prepared and hybridized as described in Examples 1, 2 and 3. Microlocation test sites were biased as in Example 3 except that the CCD camera integration was 0.5 seconds. Results showed that QATAR-1 produced approximately 60% increase in fluorescence intensity when power first applied and intensity oscillated during the entire waveform. For QATAR-5, which did not have the quencher when hybridized, there was very little fluorescence perturbation. Both QATAR 3A and 4A showed an initial increase in fluorescence approaching 40%. There was a significant decrease in intensity on QATAR-4A after bias applied. This is indicative of the lower Tm of this hybrid which had 2 mismatches. The results for QATAR 1 (match) and QATAR 3 (mismatch) are shown in FIG. 9.

Although the foregoing invention has been described in some detail by way of illustration and example for purposes of clarity and understanding, it may be readily apparent to those of ordinary skill in the art in light of the teachings of this invention that certain changes and modifications may be made thereto without departing from the spirit or scope of the appended claims.

We claim:

1. A method for hybridization analysis of a sample, the analysis utilizing an electronic stringency control device, comprising the steps of:

providing the sample, a first probe with a fluorescent label and a second probe with a label under hybridization conditions on the electronic stringency control device, forming a hybridization product, the hybridization product being attached to the electronic stringency control device, subjecting the hybridization product to a varying electric field force, simultaneously monitoring the fluorescence from the hybridization product, and analyzing the fluorescent signal.

2. The method for hybridization analysis of claim 1 wherein the fluorescence is analyzed for the fluorescent perturbation value.

3. The method for hybridization analysis of claim 2 wherein the fluorescence perturbation value is measured for the onset value.

4. The method for hybridization analysis of claim 2 wherein the fluorescence perturbation value is measured for its peak height.

5. The method for hybridization analysis of claim 2 wherein the fluorescence perturbation value is measured for its amplitude.

6. The method for hybridization analysis of claim 2 wherein the fluorescence perturbation value is measured for the slope.

7. The method for hybridization analysis of claim 2 wherein the fluorescence perturbation value is measured for its frequency.

8. The method for hybridization analysis of claim 2 wherein the fluorescence perturbation value is a measure of the rehybridization rate.

9. The method for hybridization analysis of claim 1 wherein the fluorescence is analyzed for the power level of the perturbation.

10. The method for hybridization analysis of claim 1 further including the steps of:
    determining a second measure of hybridization between the sample and the probe, and
    combining the information obtained by the first analysis including the step of subjecting the hybridization product to the varying electrophoretic force in the second measure to provide a indication of hybridization.

11. The method for hybridization analysis of claim 10 wherein the second measure of hybridization includes determination of the electronic melting point.

12. The method for hybridization analysis of claim 1 wherein the fluorescent label is placed in proximity to an initial denaturation site, a destabilization site or a site with one or more base mismatch sites.

13. The method for hybridization analysis of claim 12 wherein the fluorescent label is intercalated adjacent a single based mismatch site.

14. The method for hybridization analysis of claim 13 wherein the fluorescent label is ethidium bromide.

15. The method for hybridization analysis of claim 13 wherein the fluorescent label is acridine.

16. The method for hybridization analysis of claim 1 wherein the electrophoretic force is in an amount less than is necessary to effect complete dehybridization of the sample and the probe.

17. The method for hybridization analysis of claim 1 wherein the hybridization product is subject to an oscillating electrophoretic force.

18. The method for hybridization analysis of claim 1 wherein the electric field is a DC field.

19. The method for hybridization analysis of claim 1 wherein the electric field is an AC field.

20. The method for hybridization analysis of claim 1 wherein the electric field is sufficient to provide electrophoretic propulsive force.

21. The method for hybridization analysis of claim 1 wherein at least one label is a fluorophore.

22. The method for hybridization analysis of claim 1 wherein the fluorphore is a donor.

23. The method for hybridization analysis of claim 1 wherein at least one label is chromophore.

24. The method for hybridization analysis of claim 1 wherein the chromophore is a quencher.

25. The method for hybridization analysis of claim 1 wherein the electric field is pulsed.

26. The method for hybridization analysis of claim 25 wherein the pulse comprising a single pulse.

27. The method for hybridization analysis of claim 25 wherein the pulse comprises multiple pulses.

28. A method for achieving electronic fluorescence perturbation on an electronic stringency control device comprising the steps of:
    locating a first polynucleotide and a second polynucleotide adjacent the electronic stringency control device, the first polynucleotide and second polynucleotide being complementary over at least a portion of their lengths and forming a hybridization product, the hybridization product being attached to the electronic stringency control device, the hybridization product having an associated environmentally sensitive emissive label,
    subjecting the hybridization product and label to a varying electrophoretic force,
    monitoring the emission from the label, and
    analyzing the monitored emission to determine the electronic fluorescence perturbation effect.

29. The method for hybridization analysis of claim 28 wherein the electric field is a DC field.

30. The method for hybridization analysis of claim 28 wherein the electric field is an AC field.

31. The method for hybridization analysis of claim 28 wherein the electric field provides electrophoretic force.

32. The method for hybridization analysis of claim 28 wherein the label is a fluorophore.

33. The method for hybridization analysis of claim 28 wherein the fluorphore is a donor.

34. The method for hybridization analysis of claim 28 wherein the label is a chromophore.

35. The method for hybridization analysis of claim 28 wherein the chromophore is a quencher.

36. The method for hybridization analysis of claim 28 wherein the electric field is pulsed.

37. The method for hybridization analysis of claim 36 wherein the pulse comprising a single pulse.

38. The method for hybridization analysis of claim 36 wherein the pulse comprises multiple pulses.

39. The method for achieving electronic fluorescence perturbation of claim 28 wherein the label is a fluorophore.

40. The method for achieving electronic fluorescence perturbation of claim 28 wherein the label is a chromophore.

41. The method for achieving electronic fluorescence perturbation of claim 28 wherein the label is located within 0 to 10 bases of a base mismatch site.

42. The method for achieving electronic fluorescence perturbation of claim 28 wherein the label is located within 0 to 5 bases of a base mismatch site.

43. A method for distinguishing a match and a mismatch between a target and a probe utilizing an electronic stringency control device, comprising the steps of:
    providing a hybridization product including the sample, probe and radiation emissive label adjacent the electronic stringency control device, the hybridization product being attached to the electronic stringency control device,
    subjecting the hybridization product to an electronically stringent condition,
    monitoring the radiation emitted from the label of the hybridization product, and
    comparing the intensity of radiation at a time where a differential level of radiation emitted discriminate between a match and a mismatch.

44. The method for distinguishing a match and a mismatch between a target and a probe of claim 43 wherein the time is less than substantially 60 seconds.

45. A method for electronic perturbation catalysis of substrate molecules on an electronic control device containing at least one microlocation comprising the steps of:

immobilizing on the microlocation an arrangement of at least two catalytically reactive groups, exposing the reactive groups to a solution containing the substrate molecules of interest, and applying an electronic pulsing sequence which causes separation between the two catalytic reactive groups to produce a catalytic reaction of the substrate molecules.

46. The method for electronic perturbation catalysis of substrate molecules of claim 45 wherein the reactive groups include cysteine (thiol) and histidine (imidazole) containing catalytic peptide sequence.

* * * * *